US010264960B2

(12) United States Patent
Imamura

(10) Patent No.: US 10,264,960 B2
(45) Date of Patent: Apr. 23, 2019

(54) INFORMATION PROCESSING APPARATUS, OPERATION METHOD THEREOF, AND COMPUTER PROGRAM

(71) Applicant: CANON KABUSHIKI KAISHA, Tokyo (JP)

(72) Inventor: Hiroshi Imamura, Kyoto (JP)

(73) Assignee: Canon Kabushiki Kaisha, Tokyo (JP)

( * ) Notice: Subject to any disclaimer, the term of this patent is extended or adjusted under 35 U.S.C. 154(b) by 175 days.

(21) Appl. No.: 15/138,756

(22) Filed: Apr. 26, 2016

(65) Prior Publication Data

US 2016/0317015 A1 Nov. 3, 2016

(30) Foreign Application Priority Data

Apr. 30, 2015 (JP) ................................ 2015-093540

(51) Int. Cl.
*A61B 3/14* (2006.01)
*A61B 3/10* (2006.01)
(Continued)

(52) U.S. Cl.
CPC .......... *A61B 3/0025* (2013.01); *A61B 3/0058* (2013.01); *A61B 3/1025* (2013.01);
(Continued)

(58) Field of Classification Search
CPC ....... A61B 3/1025; A61B 3/0025; A61B 3/14; A61B 3/10; A61B 3/1233; A61B 3/0058; A61B 3/113; A61B 3/12; A61B 3/1225; A61B 5/14546; A61B 8/06; A61B 3/1015; A61B 3/102; A61B 3/00; A61B 3/0091;
(Continued)

(56) References Cited

U.S. PATENT DOCUMENTS 6,341,035 B1 * 1/2002 Miura ................ G02B 21/0044 359/363
2005/0225725 A1 * 10/2005 Warden ................ A61B 3/0075 351/216
(Continued)

FOREIGN PATENT DOCUMENTS

JP 2001-070247 A 3/2001

OTHER PUBLICATIONS

Sulai, Y., et al., "Visualization of retinal vascular structure and perfusion with a nonconfocal adaptive optics scanning light ophthalmoscope", J. Opt. Soc. Am. A, Mar. 2014, pp. 569-579, vol. 31, No. 3.

(Continued)

*Primary Examiner* — Brandi Thomas
(74) *Attorney, Agent, or Firm* — Canon USA Inc., IP Division

(57) ABSTRACT

An information processing apparatus includes: an image acquiring unit configured to acquire a plurality of types of images of an eye, including a confocal image and a non-confocal image of the eye; an analyzing unit configured to analyze the confocal image and the non-confocal image; a deciding unit configured to decide, based on analysis results of one of the confocal image and the non-confocal image, whether or not to analyze the other; and a display control unit configured to display analysis results of the confocal image and the non-confocal image on a display unit, in a case of deciding to analyze the other.

15 Claims, 12 Drawing Sheets

(51) Int. Cl.
*A61B 3/00* (2006.01)
*A61B 3/12* (2006.01)
*G02B 27/10* (2006.01)

(52) U.S. Cl.
CPC .............. *A61B 3/1233* (2013.01); *A61B 3/14* (2013.01); *G02B 27/10* (2013.01)

(58) Field of Classification Search
CPC .................. A61B 3/1241; A61B 3/152; A61B 2017/00694; A61B 3/0041
USPC ........ 351/200, 205, 206, 209–211, 221, 222, 351/243–245
See application file for complete search history.

(56) References Cited

U.S. PATENT DOCUMENTS

| | | | | |
|---|---|---|---|---|
| 2012/0062842 | A1 | 3/2012 | Griggio et al. | |
| 2013/0293841 | A1* | 11/2013 | Frison .................. | A61B 3/1025 351/206 |

OTHER PUBLICATIONS

Scoles, D., et al., "In Vivo Imaging of Human Cone Photoreceptor Inner Segments", IOVS, Jul. 2014, pp. 4244-4251, vol. 55, No. 7.

* cited by examiner

FIG. 3A
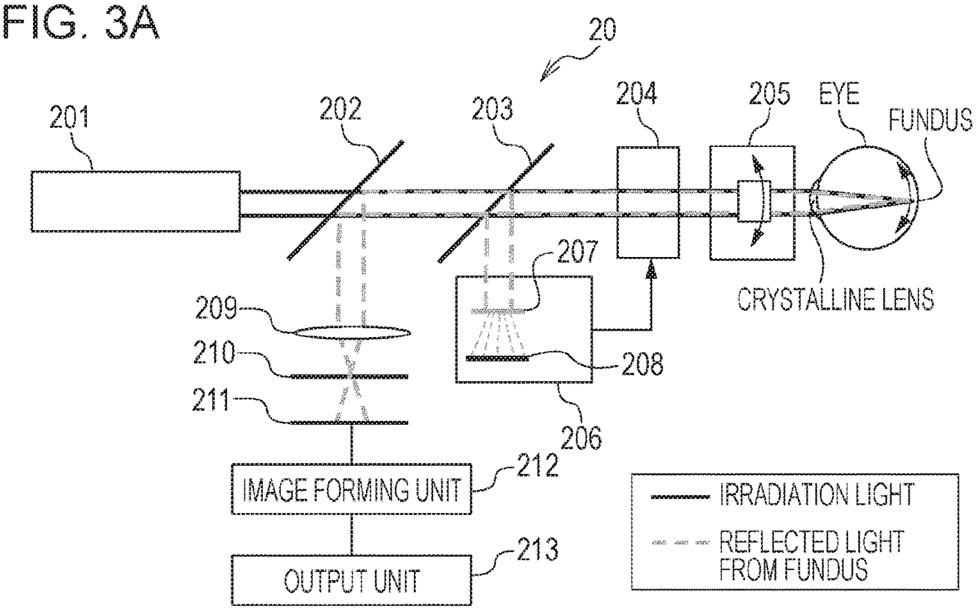
FIG. 3B
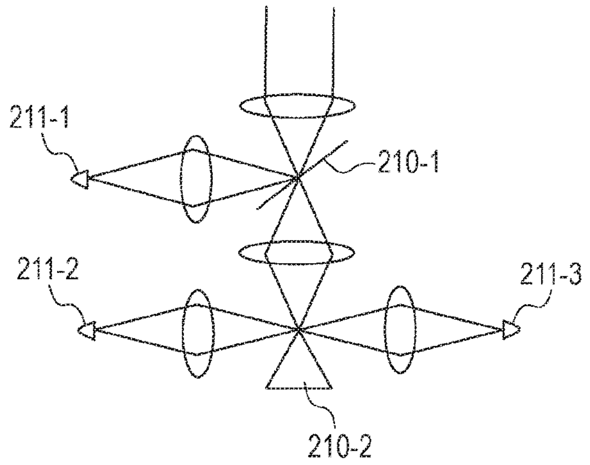
FIG. 3D FIG. 3E FIG. 3F FIG. 3G FIG. 3H
FIG. 3C
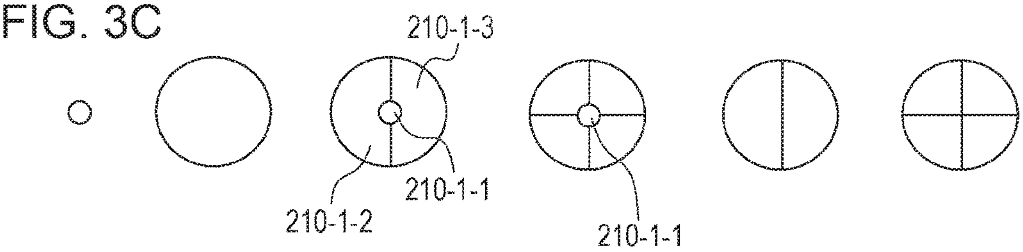

y
x
z
B1
B2
B3
B4
B5
B6 x
y
Q
P
W

DI
Pr2
Pr1

Dn11
Dn4
V
A
Dn6 x
y
Dc1
Dc3
Dc5
Dc9 x
y
Dn3
Dn1
Dn5
Dn9

VR
MP
VB
VP

INFORMATION PROCESSING APPARATUS, OPERATION METHOD THEREOF, AND COMPUTER PROGRAM

BACKGROUND OF THE INVENTION

Field of the Invention

The present invention relates to an information processing apparatus used in ophthalmological diagnosis and treatment, an operation method thereof, and a computer program.

Description of the Related Art

Examination of the eye is widely performed for early diagnosis and treatment of lifestyle diseases and diseases which are primary causes of loss of eyesight. The scanning laser ophthalmoscope (SLO), which is an ophthalmological apparatus that employs the principle of confocal laser scanning microscopy, performs high speed raster scanning of a subject's eye with a laser beam, which is measurement light, and acquires a high-resolution planar image of the fundus from the intensity of returning light.

In confocal laser scanning microscopy, detecting only light that has passed through an aperture (pinhole) enables an image to be formed just using returning light of a particular depth position (focal point), and therefore images with higher contrast than those obtained by fundus cameras and the like can be acquired. An apparatus that obtains such high-contrast planar images will hereinafter be referred to as an SLO apparatus, and a planar image obtained thusly is referred to as an SLO image.

In recent years, increased beam diameter of measurement light in SLO apparatuses has enabled acquisition of SLO images of the retina, with improved horizontal resolution. However, the increased beam diameter of the measurement light has led to deterioration of the S/N ratio and of the resolution of the SLO image during acquisition of SLO images of the retina, due to aberration of the eye being examined. An adaptive optics SLO apparatus has been developed to counter the deterioration of S/N ratio and improve resolution of the SLO image. The adaptive optics SLO apparatus has an adaptive optics system which includes a wavefront sensor and a wavefront correction device. The wave front sensor measures in real time wavefront aberrations caused by the eye being examined, and the wavefront correction device corrects the wavefront aberration with regard to the measurement light and the returning light. This enables the acquisition of SLO images with high resolution in the horizontal or main-scanning direction so that a high-magnification image can be acquired.

Such a high resolution SLO image can be acquired as a moving image. In order to noninvasively observe the dynamics of blood flow (hemodynamics), for example, retinal blood vessels are extracted from each frame of an SLO image, and the moving speed of blood cells through capillaries and so forth is measured by performing image analysis. Also, in order to evaluate the visual function of an eye using an SLO image, photoreceptors P are detected, and the density distribution and arrangement (array) of the photoreceptors P are calculated.

However, confocal images taken of the inner layers of the retina have intense noise signals due to the influence of light reflecting from the nerve fiber layer, and there have been cases where observing blood vessel walls and detection of wall boundaries has been difficult. Accordingly, as of recent, techniques have come into use for observation of non-confocal images obtained by acquiring scattered light, by changing the diameter, shape, and position of a pinhole on the near side of the light receiving portion. An example of this technique is described in Sulai, Dubra et al.; "Visualization of retinal vascular structure and perfusion with a nonconfocal adaptive optics scanning light ophthalmoscope", J. Opt. Soc. Am. A, Vol. 31, No. 3, pp. 569-579, 2014 (hereinafter "Sulai and Dubra"). Non-confocal images have a great depth of focus, so objects that have unevenness in the depth direction, such as blood vessels can be easily observed, and also noise is reduced since reflected light from the nerve fiber layer is not readily directly received. While observation of photoreceptors at the outer layers of the retina has primarily involved imaging confocal images of the outer segment of photoreceptors, it has been found that the unevenness of the inner segment of photoreceptors can be imaged in non-confocal images. This is described in Scoles, Dubra et al.; "In vivo Imaging of Human Cone Photoreceptor Inner Segment", IOVS, Vol. 55, No. 7, pp. 4244-4251, 2014 (hereinafter "Scoles and Dubra"). Sulai and Dubra disclose technology for acquiring non-confocal images of retinal blood vessels using an adaptive optics SLO apparatus, while Scoles and Dubra disclose technology for acquiring both confocal images and non-confocal images at the same time using an adaptive optics SLO apparatus. However, these known techniques lack a method of efficiently processing and analyzing confocal images and non-confocal images to accurately determine whether the confocal image and the non-confocal image yields better imaging results.

SUMMARY OF THE INVENTION

Embodiments of an information processing apparatus according to the present invention and an operation method thereof have the following configurations, for example. An information processing apparatus according to an aspect of the present invention includes: an image acquiring unit configured to acquire a plurality of types of images of an eye, including a confocal image and a non-confocal image of the eye; an analyzing unit configured to analyze the confocal image and the non-confocal image; a deciding unit configured to decide, based on analysis results of one of the confocal image and the non-confocal image, whether or not to analyze the other; and a display control unit configured to display analysis results of the confocal image and the non-confocal image on a display unit, in a case of deciding to analyze the other.

An operation method of an information processing apparatus according to an aspect of the present invention includes: a step of acquiring a plurality of types of images of an eye, including a confocal image and a non-confocal image of the eye; a step of deciding, based on analysis results of one of the confocal image and the non-confocal image, whether or not to analyze the other; and a step of displaying analysis results of the confocal image and the non-confocal image on a display unit, in a case of deciding to analyze the other.

Further features of the present invention will become apparent from the following description of exemplary embodiments with reference to the attached drawings.

BRIEF DESCRIPTION OF THE DRAWINGS

FIGS. 3A through 3H are diagrams for describing the overall configuration of an SLO image imaging apparatus according to the first embodiment.

DESCRIPTION OF THE EMBODIMENTS

SLO apparatuses that acquire confocal images and non-confocal images generally read all images into memory, and perform inter-image calculation processing or image measurement processing. This is performed in order to improve the reliability of analysis by analyzing images of different types.

It has been found desirable to effectively analyze multiple types of images of the eye, including non-confocal images of the eye, while improving reliability of analysis.

Figure 1:
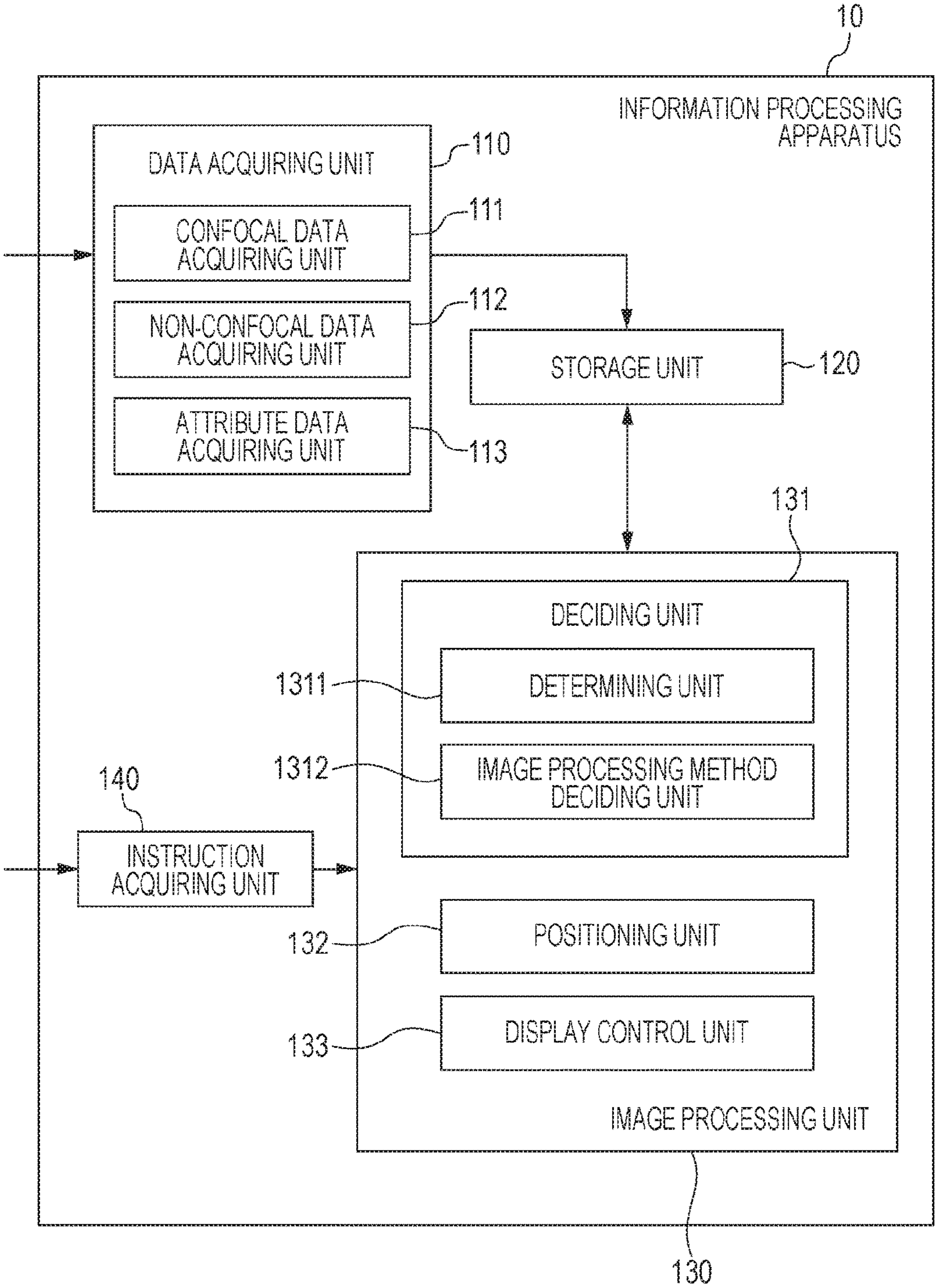
FIG. 1 is a block diagram illustrating a functional configuration example of an information processing apparatus according to a first embodiment.

Accordingly, one aspect of an embodiment includes an image acquiring unit configured to acquire multiple types of images of an eye including at least one type of non-confocal image of the eye (as an example, a data acquiring unit 110 in FIG. 1). One aspect of an embodiment includes a deciding unit 131 configured to decide an analyzing method to analyze the multiple types of images that are acquired (as an example, a deciding unit 131 in FIG. 1). One aspect of an embodiment includes an analyzing unit 130 (as an example, an image processing unit 130 in FIG. 1) configured to analyze at least one of the multiple types of images based on the decided analysis method. Accordingly, reliability of analysis can be improved while efficiently analyzing multiple types of images of the eye including at least one type of non-confocal image of the eye.

Another aspect of an embodiment includes an image acquiring unit configured to acquire multiple types of images including a confocal image and at least one type of non-confocal image of an eye (as an example, a data acquiring unit 110 in FIG. 1). Another aspect of an embodiment includes an analyzing unit configured to analyze a confocal image and at least one type of non-confocal image (as an example, the image processing unit 130 in FIG. 1). Another aspect of an embodiment includes a deciding unit configured to decide whether or not to analyze the at least one type of non-confocal image based on analysis results of the confocal image (as an example, the deciding unit 131 in FIG. 1). Another aspect of an embodiment includes a display control unit configured to display analysis results of a confocal image and at least one type of non-confocal image on a display unit, in a case of deciding to analyze the at least one type of non-confocal image (as an example, the display control unit 133 in FIG. 1). Accordingly, reliability of analysis can be improved while efficiently analyzing multiple types of images of the eye including a confocal image and at least one type of non-confocal image of the eye. Note that the deciding unit may decide whether or not to analyze the confocal image based on analysis results of the non-confocal image.

Another aspect of an embodiment preferably efficiently performs image processing upon having decided the object and method of image processing in accordance with attributes of imaged images, whether the images include anatomical features or disorder portions, and the quality of the image (image quality, and to what degree an imaging object region is included). That is to say, an apparatus that acquires multiple types of images with different light receiving methods performs image processing with priority on images which are more important with regard to observation and measurement necessitates technology of generating or measuring a great number of images more efficiently.

As noted above, the technology described in Sulai and Dubra discloses technology relating to an adaptive optics SLO apparatus that acquires multi-channel non-confocal images, bud does not disclose a method to efficiently generate or measure a great number of types of non-confocal images. Although the technology described in Scoles and Dubra acquires confocal images and non-confocal images at the same time, there is no disclosure of a method of efficiently generating or measuring confocal images and non-confocal images.

Embodiments of an image processing apparatus, an operation method thereof, and a computer program, according to the present invention, will be described below with reference to the attached drawings. It should be noted, though, that the present invention is not restricted to this description.

First Embodiment: Deciding Image Processing Method for Each Image Type Beforehand An information processing apparatus 10 according to the present embodiment is configured to uniformly perform image computation and measurement according to a method specified for each image attribute (imaging position and image type) of captured images of photoreceptors which are an example of an observation object, as necessary in observation and measurement. This is performed using an SLO apparatus which is an example of an ophthalmic imaging apparatus. Specifically, of confocal images Dc and non-confocal images Dn of photoreceptors P taken at the macular area, confocal images Dcj and Split Detector images Dnsk taken within 1.5 mm from the fovea, crucial in observation and measurement, are composited to generate composited images. In other words, images of which the center of photography is farther than 1.5 mm from the fovea, and R channel images Dnrk and L channel images Dnlk within 1.5 mm from the fovea are not used in image generation of a composite image, or in measurement of blood flow dynamics.

Overall Configuration

Figure 2A:
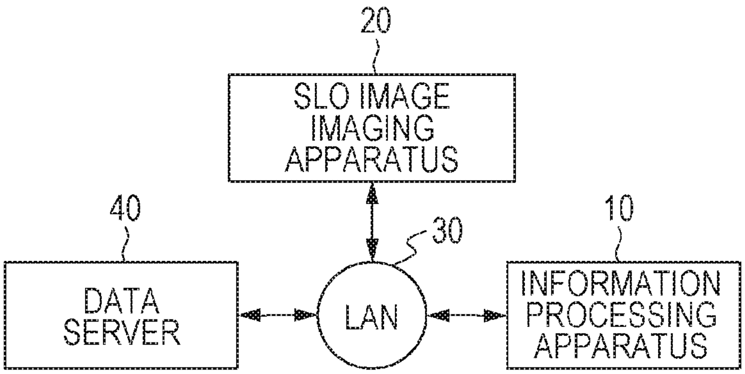
FIGS. 2A and 2B are block diagrams illustrating configuration examples of a system including the information processing apparatus according to the first embodiment.
Figure 2B:
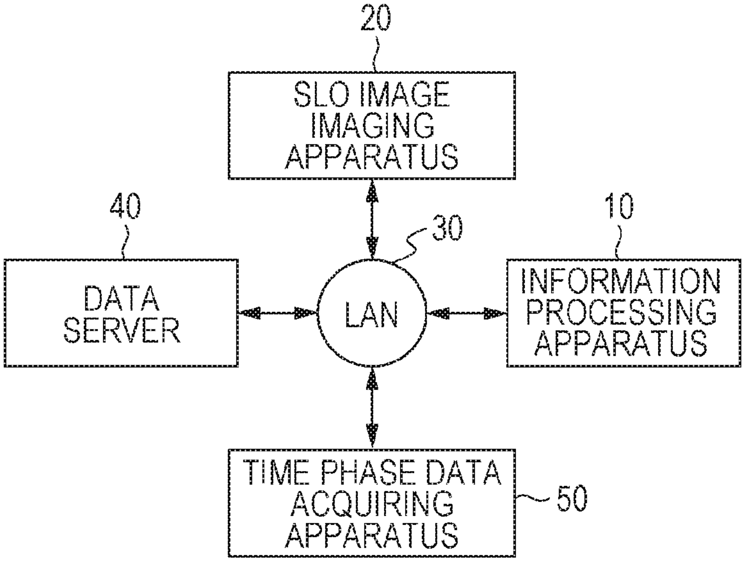

FIGS. 2A and 2B are configuration diagrams of a system including the information processing apparatus 10 according to the present embodiment. The information processing apparatus 10 is communicably connected to an SLO image imaging apparatus 20, which is an example of an ophthalmic imaging apparatus, a data server 40, and a time phase data acquisition apparatus 50, via a local area network (LAN) 30 including optical fiber, Universal Serial Bus (USB), IEEE 1394, or the like, as illustrated in FIGS. 2A and 2B. The configuration of communicable connection to these devices may be via an external network such as the Internet, or may be a configuration where the information processing apparatus 10 is directly connected to the SLO image imaging apparatus 20. Alternatively, the information processing apparatus 10 may be integrally built into an ophthalmic imaging apparatus.

The SLO image imaging apparatus 20 is an apparatus to image confocal images Dc and non-confocal images Dn, which are wide-angle images D1 and high-magnification images Dh of the eye. The SLO image imaging apparatus 20 transmits wide-angle images D1, confocal images Dc, non-confocal images Dn, and information of fixation target positions F1 and Fcn used for imaging thereof, to the information processing apparatus 10 and the data server 40. In a case where these images are acquired at different imaging positions, this is expressed as Dli, Dcj, Dnk. That is to say, i and j are variables indicating the numbers for the imaging positions, where i=1, 2, . . . , imax, j=1, 2, . . . , jmax and k=1, 2, . . . , kmax. In a case of acquiring confocal images Dc and non-confocal images Dn at different magnifications, this is expressed like Dc1*m*, Dc2*o*, . . . (Dn1*m*, Dn2*o*, . . . ) in order from the highest-magnification image, with Dc1*m* (Dn1*m*) denoting high-magnification confocal (non-confocal) images, and Dc2*o*, . . . (Dn2*o*, . . . ) denoting mid-magnification images.

The data server 40 holds the wide-angle images D1, confocal images Dc, and non-confocal images Dn, of the examinee eye, imaging conditions data such as fixation target positions F1 and Fcn used for the imaging thereof, image features of the eye, and so forth. In the present invention, image features relating to the photoreceptors P, capillaries Q, blood cells W, and retinal blood vessel walls, are handled as image features of the eye. The wide-angle images D1, confocal images Dc, and non-confocal images Dn output from the SLO image imaging apparatus 20, fixation target positions F1 and Fcn used for the imaging thereof, and image features of the eye output from the information processing apparatus 10, are saved in the server 40. Also, the wide-angle images D1, confocal images Dc, and non-confocal images Dn, and image features of the eye, are transmitted to the information processing apparatus 10 in response to requests from the information processing apparatus 10.

Figures 6A, 6B, 6C, 6D, 6E, 6F, 6G, 6H, 6I, 6J, 6K, 6L, 6M:
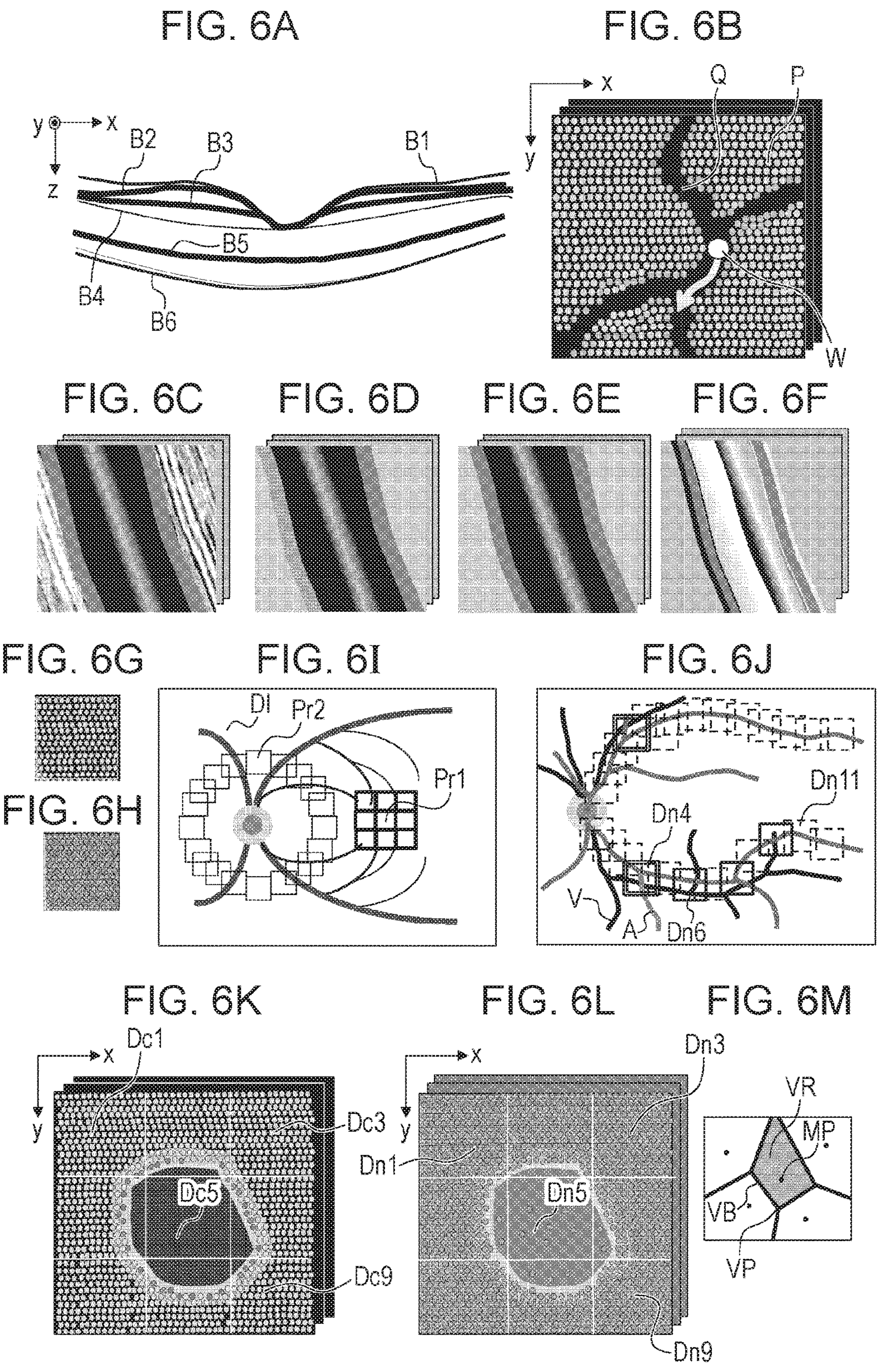
FIGS. 6A through 6M are diagrams illustrating what is performed in image processing according to the first embodiment.

FIG. 6B illustrates an example of a high resolution SLO image. In FIG. 6B, the photoreceptors P, a low-luminance region Q corresponding to the position of capillaries, and a high-luminance region W corresponding to the position of a white blood cell, can be observed. In a case of observing photoreceptors P in the SLO image, the focus position is set nearby the outer layer of the retina (B5 in FIG. 6A) to take a SLO image such as the one shown in FIG. 6B. On the other hand, there are retinal blood vessels and capillaries that have branched running through the inner layers of the retina (B2, B3 through B4 in FIG. 6A). Acquiring an SLO image with adaptive optics allows setting the focus position in the inner layers of the retina, and thus adaptive optics SLO imaging enables the retinal blood vessel walls to be directly observed.

Next, the functional configuration of the information processing apparatus 10 according to the present embodiment will be described with reference to FIG. 1. FIG. 1 is a block diagram illustrating the functional configuration of the information processing apparatus 10. The information processing apparatus 10 includes a data acquiring unit 110, a storage unit 120, an image processing unit 130, and an instruction acquiring unit 140. The data acquiring unit 110 includes a confocal data acquiring unit 111, a non-confocal data acquiring unit 112, and an attribute acquiring unit 113. The image processing unit 130 includes a deciding unit 131, a positioning unit 132, and a display control unit 133. The deciding unit 131 further has a determining unit 1311 and an image processing method deciding unit 1312.

Now, the SLO imaging apparatus 20 that applies adaptive optics will be described with reference to FIGS. 3A and 3B. The SLO imaging apparatus 20 includes a superluminescent diode (SLD) 201, a Shack-Hartman wavefront sensor 206, an adaptive optics system 204, beam splitters 202 and 203, an X-Y scanning mirror 205, a focus lens 209, a diaphragm 210, a photosensor 211, an image forming unit 212, and an output unit 213.

Light irradiated from the SLD 201 that is the light source is reflected at the fundus. Part of the reflected light is input to the Shack-Hartman wavefront sensor 206 via the second beam splitter 203, and the remaining reflected light is input to the photosensor 211 via the first beam splitter 202. Although the light source here services both as a light source for acquiring confocal images and a light source for acquiring non-confocal images, multiple light sources configured to emit different wavelengths may be used, or the like. The Shack-Hartman wavefront sensor 206 is a device to measure aberration of the eye, in which a lens eye 207 is connected to a charge-coupled device (CCD) 208. Upon input light being transmitted through the lens eye 207, bright point set appears on the CCD 208, and wave aberration is measured base on the positional gap of the projected bright points. The adaptive optics system 204 drives an aberration correction device (deformable mirror or spatial light phase modulator) to correct the aberration, based on the wave aberration measured by the Shack-Hartman wavefront sensor 206. The light subjected to aberration-correction passes through the focus lens 209 and diaphragm 210, and is received at the photosensor 211. The diaphragm 210 and photosensor 211 are examples of the aperture and optical detector according to the present invention. The aperture (of the diaphragm 210) preferably is provided upstream of and near to the optical detector (photosensor 211). The scanning position on the fundus can be controlled by moving the X-Y scanning mirror 205, thereby acquiring data according to an imaging region and time (frame rate×frame count) that the operator has instructed. The data is transmitted to the image forming unit 212, where image distortion due to variation in scanning rate is corrected and luminance value correction is performed, thereby forming image data (moving image or still image). The output unit 213 outputs the image data formed by the image forming unit 212.

The configuration of the diaphragm 210 and photosensor 211 portion in FIG. 3A is optional, just as long as the SLO imaging apparatus 20 is configured to be able to acquire confocal images Dc and non-confocal images Dn. The present embodiment is configured using a light-shielding member 210-1 (FIGS. 3B and 3E) and photosensor 211-1, 211-2, and 211-3 (FIG. 3B). Regarding the returning light in FIG. 3B, part of the light that has entered the light-shielding member 210-1 disposed at the image forming plate is reflected and enters the photosensor 211-1. Now, the light-shielding member 210-1 will be described with reference to FIG. 3E. The light-shielding member 210-1 is made up of transmitting regions 210-1-2 and 210-1-3, a light-shielded region (omitted from illustration), and a reflecting region 210-1-1, so that the center is positioned on the center of the optical axis of the returning light. The light-shielding member 210-1 has an elliptic shape pattern so that when disposed obliquely as to the optical axis of the returning light, the shape appears to be circular when seen from the optical axis direction. The returning light divided at the light-shielding member 210-1 is input to the photosensor 211-1. The returning light that has passed through the transmitting regions 210-1-2 and 210-1-3 of the light-shielding member 210-1 is split by a prism 210-2 disposed at the image forming plane, and is input to photosensors 211-2 and 211-3, as illustrated in FIG. 3B. Voltage signals obtained at the photosensors are converted into digital values at an AD board within the image forming unit 212, thereby forming a two-dimensional image. The image based on light entering the photosensor 211-1 is a confocal image where focus has been made on a particular narrow range. Images based on light entering the photosensors 211-2 and 211-3 are non-confocal images where focus has been made on a broad range. The light-shielding member 210-1 is an example of an optical member that divides returning light from the eye which has been irradiated by light from the light source, into returning light passing through a confocal region and returning light passing through a non-confocal region. The transmitting regions 210-1-2 and 210-1-3 are examples of a non-confocal region, and non-confocal images are acquired based on the returning light passing through the non-confocal regions. The reflecting region 210-1-1 is an example of a confocal region, and confocal images are acquired based on the returning light passing through the confocal region.

The method for dividing non-confocal signals is not restricted to this, and a configuration may be made where non-confocal signals are divided into four and received, such as illustrated in FIG. 3F, for example. Also, the reception method of confocal signals and non-confocal signals is not restricted to this. For example, a mechanism is preferably had where the diameter and position of the diaphragm 210 (aperture) is changeable. In doing so, at least one of the diameter of the aperture and the position in the optical axis direction is configured so as to be adjustable, so as to receive as confocal signals as illustrated in FIG. 3C and to receive as non-confocal signals as illustrated in FIG. 3D. The diameter and movement amount of the aperture may be optionally adjusted. For example, FIG. 3C shows that the diameter of the aperture can be adjusted to around 1 Airy disc diameter (ADD), and FIG. 3D shows that the diameter of the aperture can be adjusted to around 10 ADD with a movement amount of around 6 ADD. Alternatively, a configuration may be made where multiple non-confocal signals are received at the same time, as in FIGS. 3G and 3H. There are two types of non-confocal signals in the present embodiment, so one will be denoted by Dnr referring to the R channel image, and the other will be denoted by Dnl referring to the L channel image. The notation "non-confocal image Dn" refers to both the R channel image Dnr and L channel image Dnl.

The SLO imaging apparatus 20 can also operate as a normal SLO apparatus, by increasing the scan angle of the scanning optical system in the configuration in FIG. 3A, and instructing so that the adaptive optics system 204 does not perform aberration correction, so as to image wide-angle confocal images and non-confocal images. Images which are lower magnification than the high-magnification images Dc and Dn, and have the lowest magnification of images acquired by the data acquiring unit 110 will be referred to as wide-angle images Dl (Dlc, Dlr, Dll). Accordingly, a wide-angle image D1 may be an SLO image where adaptive optics has been applied, and cases of a simple SLO image are also included. Note that when distinguishing between confocal wide-angle images and non-confocal wide-angle images Dl, these are denoted by Dlc, Dlr, and Dll.

Figure 4:
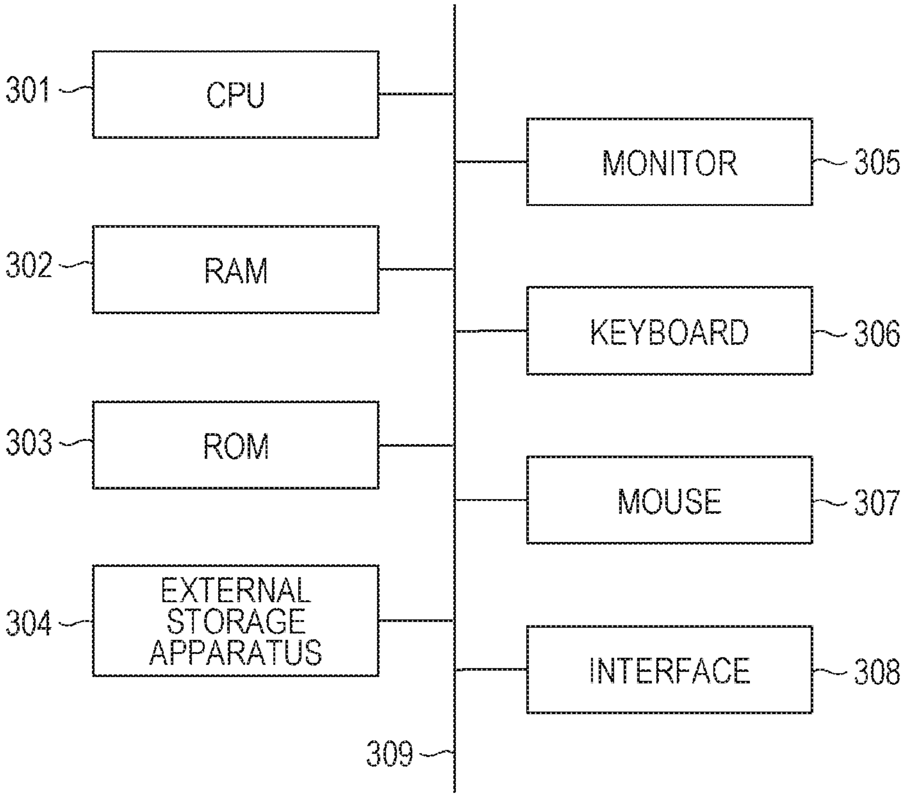
FIG. 4 is a block diagram illustrating a hardware configuration example of a computer which has hardware equivalent to a storage unit and image processing unit and holds other units as software which is executed.

Next, the hardware configuration of the information processing apparatus 10 will be described with reference to FIG. 4. In FIG. 4, 301 denotes a central processing unit (CPU), 302 memory (random access memory (RAM)), 303 control memory (read-only memory (ROM)), 304 an external storage device, 305 a monitor, 306 a keyboard, 307 a mouse, and 308 an interface. Control programs for realizing the image processing functions according to the present embodiment, and data used at the time of the control programs being executed, are stored in the external storage device 304. The control programs and data are loaded to the RAM 302 via a bus 309 as appropriate under control of the CPU 301, executed by the CPU 301, and function as the units described below. The functions of the blocks making up the information processing apparatus 10 will be correlated with specific execution procedures of the information processing apparatus 10 illustrated in the flowchart in FIG. 5.

Step S510: Image Acquisition

The image acquiring unit 110 requests the SLO imaging apparatus 20 to acquire wide-angle images D1 (Dlc, Dlr, Dll) as illustrated in FIG. 61, and high-magnification images (confocal images Dcj and non-confocal images Dnrk and Dnik) at a rectangular region in the macular area, as indicated by Pr1 in FIG. 61. Acquisition of attribute data and fixation target positions F1 and Fcn, corresponding to these images, is also requested. Attribute information in the present embodiment is date of image acquisition, position of acquisition, focus position, image type (confocal/R channel/L channel/optional inter-image-type computation), number of gradations, field angle, resolution, and number of frames. In response to this acquisition request, the SLO imaging apparatus 20 acquires the wide-angle images Dlc, Dlr, and Dll, confocal images Dcj, and non-confocal images Dnrk and Dnik, and corresponding fixation target positions Fl and Fcn, and transmits these to data acquiring unit 110. The data acquiring unit 110 receives the wide-angle images Dlc, Dlr, and Dll, confocal images Dcj, non-confocal images Dnrk and Dnik, and attribute data and fixation target positions Fl and Fcn, from the SLO imaging apparatus 20 via the LAN 30, and stores the received data in the storage unit 120. Note that the acquisition position for high-magnification images is not restricted to the rectangular region in the macular area, and images of optional acquisition positions may be used. For example, a case where an image is used that has been acquired in a ring-shaped form around the optic disc as denoted by Pr2 in FIG. 61 is also included in the present invention.

Step S520: Generating Composite Images

Figure 7A:
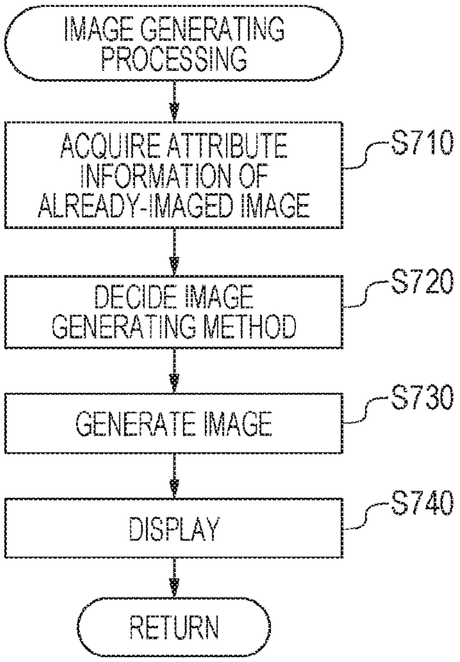
FIGS. 7A through 7C are flowcharts illustrating the details of processing executed in S520, S530, and S540 according to the first embodiment.

The determining unit 1311 determines which imaged images to use to generate a composite image, based on the attribute data of the images acquired at step S510. Next, the image processing method deciding unit 1312 decides the image generating method (type of computation between images or within images, and number of gradations, resolution, and number of frames of the image to be generated)

using the image for generation. The image processing unit 130 generates an image by performing computation within or among confocal images (Dln or Dn) by the images for generating and the image generating method decided by the determining unit 1311 and image processing method deciding unit 1312. Further, the positioning unit 132 performs image positioning, and the display control unit 133 displays confocal images and non-confocal images. Specifics of the image generating processing will be described later in detail in S710, S720, S730, and S740 of FIG. 7A.

Step S530: Deciding Measurement Method

The determining unit 1311 determines images for measurement out of the imaged and generated images, based on the attributed data of the imaged images (imaging position and image type), and the image processing method deciding unit 1312 decides a measurement method (type of image processing, range of image processing, and interval of image processing) for the images to be measured. Specifics of the measurement method deciding processing will be described later in detail in S711 and S721.

Step S540: Measurement

The image processing unit 130 performs measurement processing based on the image measurement method decided in S530, and the display control unit 133 displays the measurement results. In the present embodiment, the image processing unit 130 performs detection and distribution measurement processing of photoreceptors, and the display control unit 133 displays statistics such as photoreceptor density, along with photoreceptor positions and a Voronoi diagram. Specifics of the measurement processing will be described later in detail in S712, S722, S732, S742, and S752.

Step S550: Deciding Whether or not to Save Results

The instruction acquiring unit 140 externally acquires an instruction regarding whether or not to save in the data server 40 the images generated in S520, and the data of measurement results from S540, i.e., statistics such as photoreceptor positions, Voronoi diagram, photoreceptor density, and so forth, regarding the confocal images Dcj and non-confocal images Dnsk. This instruction is input by an operator by way of the keyboard 306 or mouse 307, for example. In a case where saving has been instructed (YES in S550) the flow advances to S560, and in a case where saving has not been instructed (NO in S550) the flow advances to S570.

Step 560: Saving Results

The image processing unit 130 correlates the examination date and information identifying the examinee eye with the images decided to be saved in S550 and data related to the measurement results, and transmits this to the data server 40.

Step 570: Decision of Whether or not to End

The instruction acquiring unit 140 externally acquires an instruction regarding whether or not to end processing of the wide-angle images Dl, high-magnification confocal images Dcj, and high-magnification non-confocal images Dnk, by the information processing apparatus 10. This instruction is input by an operator by way of the keyboard 306 or mouse 307, for example. In a case where an instruction for ending of processing is acquired (YES in S570), the processing ends. On the other hand, in a case of acquiring an instruction to continue processing (NO in S570), the flow returns to S510, and processing on the next examinee eye (or redoing the processing on the same examinee eye) is performed. The processing executed in S520 will be described in detail with reference to the flowchart in FIG. 7A.

Step S710: Acquiring Attribute Information of Imaged Image

The image processing unit 130 acquires attribute data of imaged images. Attribute information acquired in the present embodiment is date of image acquisition, position of acquisition, focus position, image type (confocal/R channel/L channel/optional inter-image-type computation such as Split Detector image), resolution, number of gradations, and number of frames.

Step S720: Deciding Image Generating Method

The determining unit 1311 determines which imaged images to use to generate an image (image for generation (acquisition position and image type)), based on the attribute data of the imaged images. Next, the image processing method deciding unit 1312 decides the image generating method (type of computation between images or within images, and number of gradations, resolution, and number of frames of the image to be generated) using the image for generation. The image processing unit 130 generates an image by performing computation within or among non-confocal images (Dln or Dn) by the images for generating and the image generating method decided by the determining unit 1311 and image processing method deciding unit 1312. Further, the positioning unit 132 performs image positioning, and the display control unit 133 displays confocal images and non-confocal images.

Specifically, in the present embodiment, the determining unit 1311 performs determination regarding images for generating already existing at the time of imaging the photoreceptors, and confocal images Dcj non-confocal images Dnk (R channel images Dnrk and L channel images Dnlk) taken within 1.5 mm from the fovea, the image processing method deciding unit 1312 makes a decision using the image for generating, so that a composited image of confocal images Dcj and a composited image of Split Detector images are generated at the same number of gradients and the same resolution as the original image. Accordingly, images of which the center of photography is farther than 1.5 mm from the fovea, and R channel images Dnrk and L channel images Dnlk within 1.5 mm from the fovea are not used in image generation or measurement. Note that a Split Detector image is a type of a differential image using non-confocal images generated by computing ((pixel value of L-channel image−pixel value of R-channel image)/(pixel value of R-channel image+pixel value of L-channel image)). The determination of the image for generating, and the deciding of the image generating method, performed at the image processing unit 130, are not restricted to the above. Any image for generating and image generating method may be used as long as an image generating method whereby detailed observation and measurement can be performed with a greater number of images for images that are crucial for observation and measurement.

Arrangements where the image for generating or the image generating method is decided based on the image attributes acquired via the instruction acquiring unit 140 are also included in the present invention. FIGS. 6G and 6H illustrate examples of a confocal image Dc and Split Detector image Dns in a case of imaging photoreceptors P.

Step S730: Generating Images

The image processing unit 130 generates an image based on the image for generating that has been determined in S720, and the image generating method that has been decided. Before generating an image, the positioning unit 132 performs inter-frame positioning of wide-angle image Dlc and confocal image Dc, and applies positioning parameter values between frames to the wide-angle images Dlr and Dll, and non-confocal images Dnr and Dnl as well. The Split Detector images Dlns and Dns are generated by computation processing of already-positioned Dlr, Dnr, and Dll, Dnl, so there is no need to perform inter-frame positioning again. Specific frame positioning methods include the following.

i) The positioning unit 132 sets a reference frame to serve as a reference for positioning. In the present embodiment, the frame with the smallest frame No. is the reference frame. Note that the frame setting method is not restricted to this, and any setting method may be used.

ii) The positioning unit 132 performs general inter-frame correlation (rough positioning). Although any positioning technique may be used, the present embodiment performs rough positioning using a correlation coefficient as an inter-image similarity evaluation function, and Affine transform as a coordinate conversion technique.

iii) The positioning unit 132 performs fine positioning based on the correspondence relation in the general position among the frames.

In the present embodiment, images that have been subjected to the rough positioning obtained in ii) are then subjected to inter-frame fine positioning, using free form deformation (FFD), which is a type of a non-rigid positioning technique. Note that the fine positioning technique is not restricted to this, and any positioning technique may be used. After image generation, the positioning unit 132 positions wide-angle image Dlc and high-magnification image Dcj, and finds the relative position of Dcj on Dlc. The positioning unit 132 acquires the fixation target position Fcn used at the time of imaging the high-magnification confocal images Dcj from the storage unit 120, to use as the initial point for searching for positioning parameters for the positioning of the wide-angle image Dlc and confocal image Dcj. The positioning of the wide-angle image Dlc and high-magnification confocal image Dcj is performed while changing combinations of the parameter values. The combination of parameter values where the similarity between the wide-angle image Dlc and high-magnification confocal image Dcj is highest is decided to be the relative position of the confocal image Dcj as to the wide-angle image Dlc. Note that the positioning technique is not restricted to this, and any positioning technique may be used.

Also, in a case where a mid-magnification image has been acquired in S510, positioning is performed from images with lower magnification. For example, in a case where a high-magnification confocal image Dc1*m* and a mid-magnification image Dc2*o* have been acquired, first, the wide-angle image Dlc and the mid-magnification image Dc2*o* are positioned, and next, the mid-magnification image Dc2*o* and the high-magnification confocal image Dc1*m* are positioned.

Further, image tiling parameter values decided regarding the wide-angle confocal image Dlc and confocal image Dcj are applied to tiling of the non-confocal images Dlr and Dnrk, Dll and Dnlk, Dlns and Dnsk) as well. The relative positions of the high-magnification non-confocal images Dnrk, Dnlk, and Dnsk on the wide-angle non-confocal images Dlr, Dll, and Dlns are each decided.

Step 740: Display

The display control unit 133 displays the generated image group on the monitor 305. An image obtained by compositing the confocal image Dcj and Split Detector image Dnsk determined to be images for generating in S720 (images of which the center of photography is within 1.5 mm from the fovea) are tiled here using the positioning parameter values decided in S730, and displayed. The type of images to be display is switched using a graphical user interface (GUI) that has been prepared for this purpose. Although radio buttons are used for switching in the present embodiment, any GUI arrangement may be used for the switching. The types of images to be switched are the two types of confocal image Dc and Split Detector image Dns.

Figure 7B:
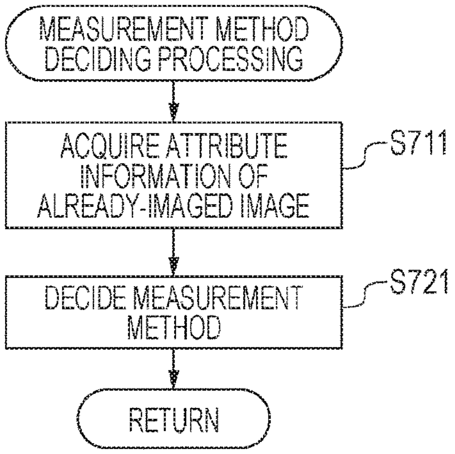

Now, the processing executed in S530 will be described in detail with reference to the flowchart of FIG. 7B.

Step S711: Acquiring Attribute Information of Imaged Image

The image processing unit 130 references the attribute data in the imaged images acquired in S710.

Step S721: Decide Measurement Method

The determining unit 1311 determines images to measure (acquisition position and image type), based on the attribute data of the imaged images acquired in S711. Next, the image processing method deciding unit 1312 decides the measurement method (type of image processing, range of image processing, intervals of image processing) regarding the images to measure.

The determining unit 1311 determines confocal images Dcj and Split Detector images Dnsk of which the center of photography is within 1.5 mm from the fovea to be the present measurement object at the time of imaging photoreceptors. That is to say, images of which the center of photography is farther than 1.5 mm from the fovea, and R channel images Dnrk and L channel images Dnlk within 1.5 mm from the fovea are not the object of measurement. The image processing method deciding unit 1312 decides to perform the following image processing on the composited image of confocal images Dcj and Split Detector images Dnsk of which the center of photography is within 1.5 mm from the fovea.

Detection of photoreceptor position

Creating a Voronoi diagram

Measuring photoreceptor density

There is the need to perform measurement on two types of images and compare the measurement results under the same conditions in the present embodiment, so the image processing range and image processing interval (intervals between measurement positions) are the same range, the same image size, and same distance for both images as the original image. The present invention is not restricted to this, and any image processing range and image processing interval values may be set to the images, as long as the processing is capable of measuring images crucial for measurement in a more detailed manner.

Figure 7C:
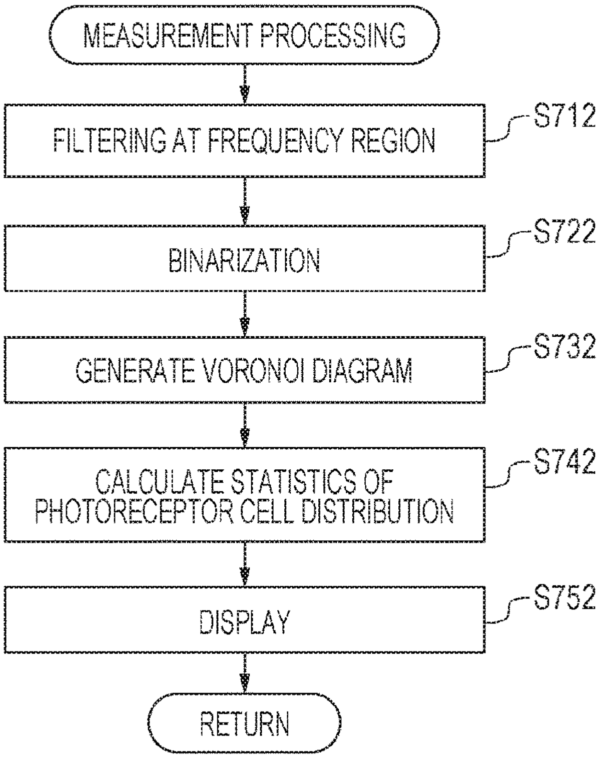

Further, the processing executed in S540 will be described in detail with reference to the flowchart in FIG. 7C.

Step S712: Filtering in Frequency Region

The image processing unit 130 removes high-frequency components, to remove peak components other than the photoreceptors in the confocal images Dcj and non-confocal images Dnsk (noise and reflected light from fundus tissue other than photoreceptors). The present embodiment performs frequency conversion using fast Fourier transform (FFT), and cuts out high-frequency component signal value by applying a low-pass filter. The filtered images are restored to space domain by inverse Fourier transform, thereby generating corrected confocal images and corrected non-confocal images with the high-frequency component removed.

Step S722: Binarization

The photoreceptors P are detected by binarizing the corrected confocal images and corrected non-confocal images using threshold values Tc and Ts, respectively.

Step S732: Generating Voronoi Diagram

A Voronoi diagram is generated for the binarized image of the photoreceptors P, following the procedures below. The center point of each photoreceptor region (MP in FIG. 6M) is calculated for the binarized image of photoreceptors P, and a perpendicular bisector is drawn for each line segment connecting a center point MP with an adjacent center point MP. The drawn perpendicular bisectors from the median point of the line segments connecting the center points MP up to intersections VP with other perpendicular bisectors are retained and all other bisectors are erased, thereby obtaining Voronoi boundaries VB. The areas and shapes that the individual photoreceptors P have are represented by regions VR enclosed by the Voronoi boundaries VB.

Step S742: Calculating Statistics of Photoreceptor Distribution

Statistics relating to the distribution of photoreceptors P are calculated based in the Voronoi diagram generated in S732. Specifically, the density of the detected photoreceptors P, the average distance between adjacent photoreceptors, the average value of area that each photoreceptor occupies, the rate of region where photoreceptors P are expressed in the form of hexagons in the Voronoi diagram, are calculated. Note that the Statistics are calculated not only for the overall image but also for each small region.

Step S752: Display

The display control unit 133 displays on the monitor 305:

i) corrected confocal images and corrected non-confocal images ii) detection results of photoreceptors P iii) Voronoi diagram iv) map relating to statistics on photoreceptor distribution for each small region.

The Voronoi diagram is displayed with each Voronoi region colored in accordance with area. Note that the present embodiment has been described with regard to an arrangement where the deciding unit 131 decides methods for inter-image computation, image feature extraction (photoreceptor detection, blood vessel wall boundary detection, etc.), and image measurement, uniformly by methods specified for each imaging position and image type, as necessary for observation and measurement, but the present invention is not restricted to this. For example, arrangements where the determining unit 1311 in the deciding unit 131 uniformly determines which images are to be read into the storage unit 120, and which images are to be displayed on the monitor 305, by methods specified for each imaging position and image type, as necessary for observation and measurement, are also included in the present invention. Alternatively, the image processing method deciding unit 1312 may uniformly decide methods to display images (resolution, number of gradients, number of frames (including deciding whether moving image or still image), etc.), by methods specified for each imaging position and image type, as necessary for observation and measurement.

According to the configuration described above, the information processing apparatus 10 uniformly performs image computation and calculation uniformly by methods specified for each image attribute (imaging position and image type), as necessary for observation and measurement, on images where photoreceptors have been imaged using the SLO apparatus that acquires confocal images and non-confocal images at the same time. Accordingly, images of the eye that are crucial for observation and measurement can be efficiently generated or measured.

Although analyzing methods (example of image processing methods) are decided beforehand for each of multiple types of images, a configuration may be made where the analyzing method can be changed for each of the multiple types of images in accordance with user specification (e.g., selecting an image processing method). Different analyzing methods are preferably selected for each of the multiple image types. For example, confocal images may be given priority over non-confocal images, and at this time, an analyzing method may be decided that the non-confocal images are not analyzed. Conversely, non-confocal images may be given priority over confocal images, and at this time, an analyzing method may be decided that the confocal images are not analyzed. Further, the decided analyzing methods preferably include a method where the images are not analyzed. That is to say, deciding the analyzing method preferably includes deciding whether or not to analyze images. These are also applicable to the following embodiments.

Second Embodiment: Deciding Image Processing Method by Feature Regions in Image An information processing apparatus according to a second embodiment performs the following processing on images taken with an SLO apparatus that acquires confocal images and non-confocal images at generally the same time. The information processing apparatus is configured so that, based on image features or disorder candidate regions, the more crucial a portion for observation or image analysis included in an image is, the wider the variety or greater the detail of images that are generated is, or a wider variety of images are measured. Specifically, an SLO apparatus such as illustrated in FIGS. 3A and 3B that acquires confocal images Dcj and non-confocal images Dnk at generally the same time, acquires confocal images Dcj and non-confocal images Dnk of retinal blood vessels at acquisition positions such as illustrated in FIG. 6J. Although a region where an initial disorder has damaged the outer segment but the inner segment has survived, this is imaged as a black defect area in confocal images (Dc5 in FIG. 6K), but can be observed as a region where high-luminance granular objects exist in non-confocal images (Dn5 in FIG. 6L). A case will be described where the more arteriovenous crossing portions, which are areas of predilection for retinal vein occlusion, are included in an image, the wider the variety or greater the detail of images that are generated is, or a wider variety of images are measured.

FIG. 2B illustrates the configuration of an apparatus connected to the information processing apparatus 10 according to the present embodiment. The present embodiment differs from the first embodiment in that the information processing apparatus 10 is connected to a time phase data acquisition apparatus 50, in addition to the SLO imaging apparatus 20. The time phase data acquisition apparatus 50 is an apparatus that acquires biosignal data (time phase data) that autonomously and cyclically changes, such as a sphygmograph or electrocardiograph, for example. The time phase data acquisition apparatus 50 acquires time phase data Sj at the same time as acquiring high-magnification images Dnk, in accordance with operations performed by an unshown operator. The acquired time phase data Sj is sent to the information processing apparatus 10 and data server 40. Note that the time phase data acquisition apparatus 50 may be directly connected to the SLO imaging apparatus 20.

In addition to the wide-angle images Dlr and Dll and high-magnification images Dnrk and Dnlk of the examinee eye, and acquisition conditions such as the fixation target positions Fl and Fcn used at the time of acquisition, the data server 40 also holds image features of the eye. Any image features of the eye may be used, but the present embodiment handles retinal blood vessels and capillaries Q, and photoreceptor damage regions. The time phase data Sj output from the time phase data acquisition apparatus 50 and image features output from the information processing apparatus 10 are saved in the server. The time phase data Sj and image features of the eye are transmitted to the information processing apparatus 10 upon request by the information processing apparatus 10.

Figure 8:
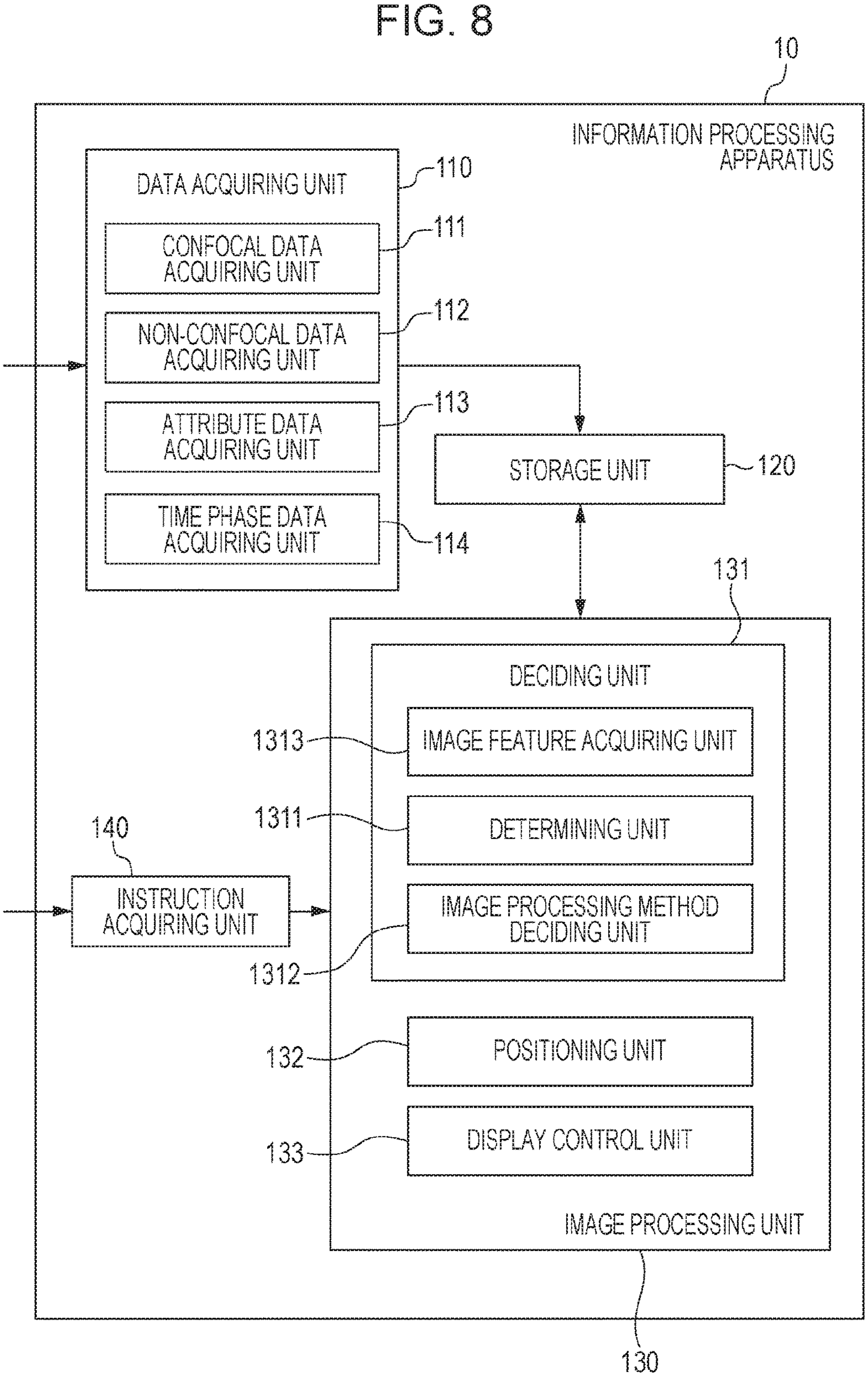
FIG. 8 is a block diagram illustrating a functional configuration example of an information processing apparatus according to a second embodiment.

Next, FIG. 8 illustrates a functional block diagram of the information processing apparatus 10 according to the present embodiment. This configuration differs from the first embodiment with regard to the point that the data acquiring unit 110 has a time phase acquiring unit 114, and the deciding unit 131 has an image feature acquiring unit 1313. The image processing flow according to the present embodiment is the same as that illustrated in FIG. 5. Other than S510, S520, S530, and S540, the flow is the same as in the first embodiment, so just the processing of S510, S520, S530, and S540 will be described in the present embodiment.

Step S510: Image Acquisition

The data acquiring unit 110 acquires wide-angle images Dlc and Dln, confocal images Dcj, non-confocal images Dnk, and time phase data. Confocal images Dcj and non-confocal images Dnk are acquired following a retinal artery arcade A in the present embodiment, as illustrated in FIG. 6J. The time phase acquiring unit 114 requests the time phase data acquisition apparatus 50 for time phase data Sj relating to biological signals. In the present embodiment, a sphygmograph serves as a time phase data acquisition apparatus, used to acquire pulse wave data Sj from the earlobe of the subject. This pulse wave data Sj is expressed with acquisition time on one axis and a cyclic point sequence having the pulse wave signal values measured by the sphygmograph on the other axis. The time phase data acquisition apparatus 50 acquires and transmits the time phase data Sj corresponding to the acquisition request. The time phase acquiring unit 114 receives this pulse wave data Sj from the time phase data acquisition apparatus 50 via the LAN 30. The time phase acquiring unit 114 stores the received time phase data Sj in the storage unit 120.

Now, there are two conceivable timings relating acquisition of the time phase data Sj by the time phase data acquisition apparatus 50; one is a case where the confocal data acquiring unit 111 or image processing method deciding unit 1312 starts image acquisition in conjunction with a particular phase of the time phase data Sj, the other is a case where acquisition of pulse wave data Pi and image acquisition are simultaneously started immediately after an image acquisition request. In the present embodiment, acquisition of pulse wave data Pi and image acquisition are simultaneously started immediately after an image acquisition request. The time phase data Pi of each image is acquired by the time phase acquiring unit 114, the extreme value in each time phase data Pi is detected, and the cardiac cycle and relative cardiac cycle are calculated. The relative cardiac cycle is a relative value represented by a floating-point number between 0 and 1 where the cardiac cycle is 1. The data acquiring unit 110 requests the SLO imaging apparatus 20 for acquisition of wide-angle images Dlc, Dlr, and Dll, confocal images Dcj, non-confocal images Dnrk and Dnlk, and corresponding fixation target position F1 and Fcn data.

In response to the request, the SLO imaging apparatus 20 acquires and transmits the wide-angle images Dlc, Dlr, and Dll, confocal images Dcj, non-confocal images Dnrk and Dnlk, and corresponding fixation target positions F1 and Fcn. The data acquiring unit 110 receives the wide-angle images Dlc, Dlr, and Dll, confocal images Dcj, non-confocal images Dnrk and Dnlk, and corresponding fixation target positions Fl and Fcn, from the SLO imaging apparatus 20 via the LAN 30, and stores these in the storage unit 120. FIGS. 6C and 6D illustrate an example of a confocal image Dc and non-confocal image Dnr in a case of having photographed a retinal blood vessel. The confocal image Dc has strong reflection from the nerve fiber layer, so the background noise makes positioning difficult. The non-confocal image Dnr (Dnl) of the R channel (L channel) has higher contrast at the blood vessel wall at the right side (left side).

On the other hand, examples of non-confocal images are not limited to this. Other examples include an addition process image Dnr+l of non-confocal images Dnr and Dnl, and a Split Detector images Dns to which a type of differential processing ((L−R)/(R+L)) has been applied. FIGS. 6E and 6F illustrate examples of Dnr+l and Dns. "Non-confocal image Dnk" below can refer to any of these non-confocal images Dnk.

Step S520: Generating Images

The image feature acquiring unit 1313 acquires retinal blood vessel regions and arteriovenous crossing portions as image features from the wide-angle images Dln. Although the image features are acquired in S520 in the present embodiment, acquiring the image features in this step is not restrictive. For example, cases where the image features are acquired immediately after image acquisition in S510, and cases where the image features are acquired in S530, are also included in the present invention. Next, determination is made regarding which imaged image (image for generating) to use to generate an image is determined by the determining unit 1311 based on the image features. Further, the image processing method deciding unit 1312 determines the image generating method (type of inter-image or intra-image computation, and number of gradients, resolution, and number of frames of generated image) based on the image features. Further, the image processing unit 130 performs computation among non-confocal data (Dln or Dn) according to the computation contents decided by the image processing method deciding unit 1312 to generate images, and the positioning unit 132 executes image positioning. The display control unit 133 displays confocal images and non-confocal images. Specific image generating processing will be described in detail in S910, S920, S930, and S940.

Step S530: Deciding Measurement Method

The determining unit 1311 determines images to be measured (imaging position and image type) from the images that have been imaged and generated, based on the image features (retinal blood vessel regions and arteriovenous crossing portions) acquired by the image feature acquiring unit 1313 in S520. Further, the image processing method deciding unit 1312 decides the measurement method for the images to be measured (type of image processing, range of image processing, and interval of image processing) for the images to be measured, based on the image features. Specifics of the measurement method deciding processing will be described later in detail in S911 and S921.

Step S540: Measurement

The image processing unit 130 performs measurement processing based on the image measurement method decided in S530, and the display control unit 133 displays the measurement results. In the present embodiment, the image processing unit 130 detects retinal blood vessel walls and performs wall thickness measurement processing, and the display control unit 133 displays detected wall boundaries, wall thickness graphs, and wall thickness maps. Specifics of the measurement processing will be described later in detail in S912, S922, S932, and S942.

Figure 9A:
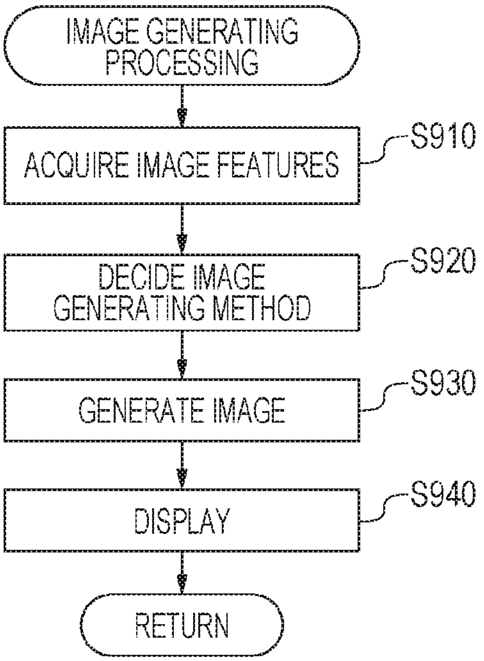
FIGS. 9A through 9C are flowcharts illustrating the details of processing executed in S520, S530, and S540 according to the second embodiment.

Next, the processing executed in S520 will be described in detail with reference to the flowchart in FIG. 9A.

Step S910: Image Feature Acquisition

The image feature acquiring unit 1313 detects the retinal blood vessel regions and arteriovenous crossing portions as image features from the wide-angle images Dln. The images from which image features are acquired are not restricted to wide-angle images, and cases of directly acquiring image features from high-magnification images Dnk, for example, are also included in the present invention. Retinal blood vessels have linear shapes, so the present embodiment employs a retinal blood vessel region detection method where a filter that enhances linear structures is used to extract the retinal blood vessels. Specifically, a wide-angle image Dln is smoothed by a Gaussian function of a size σ equivalent to the radius of the arcade blood vessel, and thereupon a tube enhancement filter based on a Hessian matrix is applied, and binarization is performed at a threshold value Ta, thus extracting the arcade blood vessels.

As for the method for detecting arteriovenous crossing portions in the present embodiment, a crossing detection filter disclosed in Japanese Patent Laid-Open No. 2001-070247 is used. Specifically, a crossing portion is determined when there are four or more blood vessel regions at the perimeter of the filter, and there is a blood vessel region at the center portion of the filter. Retinal arteries contain more hemoglobin than retinal veins and thus are higher in luminance, so the lowest luminance value within each of the crossing blood vessel regions is calculated from the detected crossing portions, and in a case where the absolute value among the lowest luminance values is equal to or larger than a threshold value T1, this is determined to be an arteriovenous crossing. Note however, that the crossing detection method is not restricted to this, and any known crossing detection method may be used. Retinal veins tend to be lower with regard to luminance distribution of the intravascular space region (the region where blood flows), so in the present invention, if the lowest luminance value in the intravascular space region in confocal images and non-confocal images is smaller than Tv, this is identified as a retinal vein in the present invention, and if Tv or larger, as a retinal artery.

Although description has been made in the present embodiment that the image feature acquiring unit 1313 acquires anatomical features such as arteriovenous crossing portions, the present invention is not restricted to this. For example, a disorder candidate region such as the photoreceptor defect portion Dc5 in FIG. 6K may be acquired as an image feature. Although any detection method of the photoreceptor defect region may be used, detection is made in the present embodiment according to the following procedures. That is to say, Fourier transform is performed in the confocal images Dcj, a low-pass filter is applied to cut out high-frequency signal values, following which inverse Fourier transform is performed, and each region having a value smaller than a threshold T2 is detected as a photoreceptor defect region.

Step S920: Deciding Image Generating Method

The determining unit 1311 determines which imaged image (image for generating) to use to generate an image, based on the image features acquired by the image feature acquiring unit 1313 in S910. Further, the image processing method deciding unit 1312 decides the image generating method (type of computation between images or within images, and number of gradations, resolution, and number of frames of the image to be generated), based on the image features. In retinal vein occlusion, which is a common eye disorder, arteriovenous crossing portions are an area of predilection (blockage of retinal veins), so in the present embodiment, images including arteriovenous crossing portions are used to generate images with large total data amounts (many types of images or images with large data amount). Specifically, the determining unit 1311 determines an image including a retinal blood vessel area to be an image for generating. The image processing method deciding unit 1312 decides the image type for generating to be a (R+L) image Dnr+l. The image processing method deciding unit 1312 further decides to generate, with regard to an image including an arteriovenous crossing portion, a moving image having the same resolution as the original image in 16-bit and a composited image having the same resolution as the original image in 16-bit, and with regard to an image not including an arteriovenous crossing portion, a composited image having the same resolution as the original image in 16-bit. However, this is not restrictive, and any image type to be generated and any generating method thereof may be specified, as long as an image generating method that enables a greater number of images to be observed and measured in detail with regard to images that are crucial for observation and measurement. For example, the image processing method deciding unit 1312 may decide the image type to be generated to be (R+L) images Dnr+l and Split Detector images Dns for images including arteriovenous crossing portions, and just (R+L) images Dnr+l for images not including arteriovenous crossing portions.

In a case of acquiring a disorder region (disorder candidate) which is an example of a state that is the object of observation, such as photoreceptors of the eye, as image features from a confocal image Dc in step S910, the image for generating is decided according to the following procedures. A photoreceptor defect region, which is an example of a disorder region, will be described here. It is generally understood that photoreceptors, which are an example of observation, become defective from the outer segments, next become defective at the inner segments, and finally reach necrosis. Scoles and Dubra describe that confocal images Dcj enable photoreceptor outer segment defects to be observed, while non-confocal images Dnk enable photoreceptor inner segment defects to be observed. Accordingly, it can be understood that photoreceptor defect regions in confocal images (at least images including photoreceptor outer segment defects) and Split Detector images at the same imaging position, are important for observation and analysis of the level of the photoreceptor disorder. Thus, the determining unit 1311 determines, from the imaged images, confocal images at all imaging positions, and non-confocal images Dn at the same imaging positions as confocal images containing photoreceptor defect regions in the confocal images, to be images for generating (imaging position and image type). Further, the image processing method deciding unit 1312 further decides to generate a composited image having the same resolution as the original image in 16-bit, for all confocal images Dcj, regardless of whether or not a photoreceptor detect region is included, and a Split Detector image Dnsk using a generating R channel image Dnrk and L channel image Dnlk in 16-bit and as a composited image having the same resolution as the original image in 16-bit. However, this is not restrictive, and any image type to be generated and any generating method thereof may be specified, as long as an image generating method that enables a greater number of images to be observed and measured in detail with regard to images that are crucial for observation and measurement.

Step S930: Generating Images

The image processing unit 130 generates images by performing computation among non-confocal images (Dln or Dn) according to the computation decided by the image processing method deciding unit 1312, and the positioning unit 132 executes image positioning. In the present embodiment, the image processing unit 130 generates (R+L) images (Dlnr+l and Dnr+l). Computation by the image processing unit 130 is not restricted to this, and any computation processing may be performed. The positioning unit 132 performs inter-frame positioning and compositing of generated wide-angle images Dlr+l and non-confocal images Dnr+l, and further performs tiling processing of composited wide-angle images Dlr+l and composited high-magnification images Dn(r+l)k. Moreover, the display control unit 133 displays the generated image group on the monitor 305. Specific inter-frame positioning and tiling procedures are the same as in the first embodiment, and accordingly description will be omitted here. The inter-frame positioning parameters decided here are also applied to the wide-angle images Dlr, Dll, and Dlc, and high-magnification images Dnr, Dnl, and Dc, that have the same imaging position. In the same way, the image tiling parameter values decided with regard to the wide-angle images Dlr+l and non-confocal images Dnr+l are applied to tiling of confocal images (Dlc and Dcj) and tiling of non-confocal images (Dlr, Dnrk, and Dnlk) as well.

On the other hand, with regard to measurement of blood vessel wall thickness, composited images are generated according to the following procedures to avoid change in the shape of the blood vessels among frames due to influence of the heartbeat. That is to say, instead of averaging all frames, just frames correlated with pulse wave signals belonging to a particular phase interval are selected and composited. In the present embodiment, the phase intervals of pulse waves are divided into five intervals, and the frames belonging to the interval including the phase where the pulse wave signal value is minimal are selected and composited. However, the frame selection method is not restricted to this, and any selection method can be used yields the effects of eliminating the influence of the heartbeat can be used.

Step S940: Display

The display control unit 133 displays the generated images. In this case, the images generated in S930 are tiled using the positioning parameters described above, and displayed.

Figure 9B:
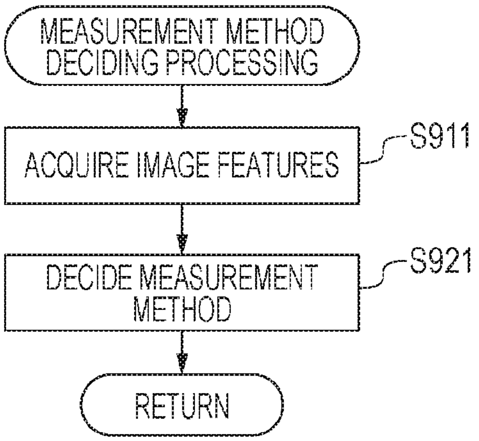

The processing performed in S530 will be described in detail with reference to the flowchart illustrated in FIG. 9B.

Step S911: Acquiring Image Features

The image processing method deciding unit 1312 references the image features acquired by the image feature acquiring unit 1313 in S910 (retinal blood vessel regions and arteriovenous crossing portions, or the photoreceptor defect portion Dc5).

Step S921: Deciding Measurement Method

The determining unit 1311 performs determination (imaging position and image type) of the images that are objects of measurement, based on image features acquired in S911. Next, the image processing method deciding unit 1312 decides the image measurement method (type of image processing, range of image processing and intervals of image processing) for the images that are objects of measurement. In retinal vein occlusion, which is a common eye disorder, arteriovenous crossing portions are an area of predilection (blockage of retinal veins), so in the present embodiment, detailed measurement processing is performed regarding images including arteriovenous crossing portions. Specifically, the determining unit 1311 determines images including a retinal blood vessel area to be images for measuring. Next, the image processing method deciding unit 1312 decides Edge preservation smoothing processing Blood vessel wall boundary detection Blood vessel wall thickness measurement to be types of image processing to be performed on the (R+L) images Dr+l at imaging positions including arteriovenous crossing portions, out of the measurement methods for the images to be measured. With regard to the range of image processing, edge preservation smoothing is performed for the entire image, and blood vessel wall boundary detection and blood vessel wall thickness measurement are decided only for arterial branches crossing veins. As for images that do not include arteriovenous crossing portions, just edge preservation smoothing processing is applied as a type of image processing to the entire image every two pixels, and measurement processing is not applied. However, this is not restrictive, and any determining processing for the images to be measured and deciding processing for the image processing method may be specified, as long as an image processing method that enables a greater number of images to be measured or measured in detail with regard to images having image features that are crucial for measurement. Note that in a case of acquiring disorder candidates such as a photoreceptor defect region from the confocal images Dcj and non-confocal images Dnk as image features in S911, the measurement method is decided according to the following procedures.

In the same way as in S920, a Split Detector image having the same imaging position as a photoreceptor defect region in a confocal image can be though to be a crucial image in observing and analyzing the degree of the photoreceptor disorder. Accordingly, the determining unit 1311 determines confocal images containing a photoreceptor defect region and Split Detector images having the same imaging position as the confocal images, out of the images that have been imaged and generated, to be images to be measured (imaging position and image type). That is to say, confocal images Dc that do not contain a photoreceptor defect region are determined not to be the object of measurement. Further, based on the image features, the image processing method deciding unit 1312 decides, as the image measurement method (type of image processing, range of image processing, and interval of image processing) for the images that are objects of measurement, Detection of photoreceptor position Creating a Voronoi diagram Measuring photoreceptor density so that all images a processed over the same range as the original image, in one-pixel intervals. However, this is not restrictive, and any type of image processing, range of image processing, and interval of image processing may be specified for each image, as long as processing that enables a wider variety of images to be measured or measured in detail with regard to images having image features that are crucial for measurement.

Figure 9C:
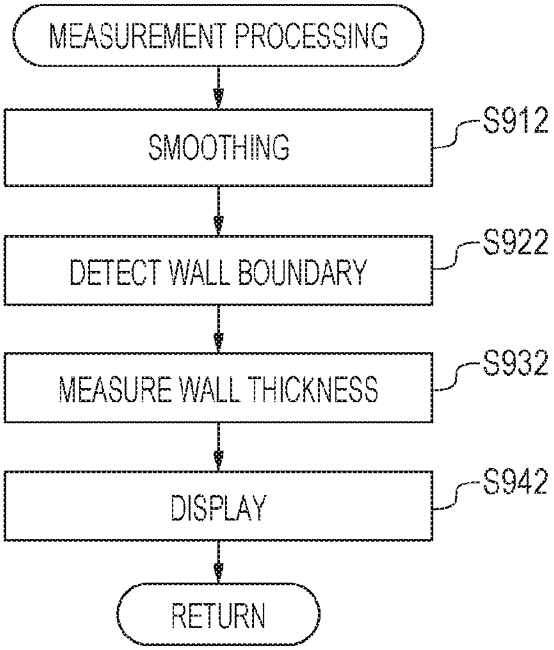

Next, the processing performed in S540 will be described in detail with reference to the flowchart illustrated in FIG. 9C.

Step S22: Smoothing

The image processing unit 130 performs smoothing processing on the image to be measured. Although any known edge preservation smoothing processing may be applied, in the present embodiment a median value filter is applied in one-pixel intervals to the entire image of composited images of (R+L) images including arteriovenous crossing portions. On the other hand, the median filter is applied in two-pixel intervals to the entire image of images containing other blood vessel regions. This edge preservation smoothing processing enables noise within the image to be reduced without blurring the edges of blood vessel wall boundaries.

Step S922: Detecting Wall Boundaries

The image processing unit 130 detects boundary positions of retinal arteries. First, a Top-hat filter, which is a type of morphology filter, is applied to the smoothed image generated in S912. By applying the Top-hat filter, a slender high-luminance region that is present near the center of a blood vessel (blood column reflection) is extracted, and thereafter the extracted region is formed into a fine line, thereby detecting the center line of the artery. Note that “Top-hat filter processing” refers to is processing where luminance values of an opening image (an image where the original image is subjected to reduction processing and then to expansion processing) are subtracted from the luminance values of the original image. The Top-hat filter may be applied to an image obtained by the original image having been binarized, or a multi-value Top-hat filter may be applied to the original image and then binarization performed. The method for detecting the center line of the blood vessel is not restricted to this, and any known method may be used.

Next, luminance profiles are generated on line segments that pass through control points set equidistantly on the center line and are generally perpendicular to the center line. Two maximum values each are extracted for the left side of the line segment from the center and for the right side of the line segment from the center, and these are taken as the blood vessel wall boundaries. Note that the blood vessel wall boundary detection method is not restricted to this, and any known technique may be used. For example, the following technique may be used. Four cures parallel to the center line of the blood vessel are generated, with two curves disposed on the intravascular space region, and two are disposed on the outside of the blood vessel, as a deformable model. Minimizing an evaluation function stipulated regarding shapes between control points making up the model and luminesce values on the control points results in the four deformable models being deformed to match the blood vessel wall boundaries, thereby detecting the blood vessel wall boundary positions.

Step S932: Measuring Wall Thickness

The image processing unit 130 calculates the outer diameter of the blood vessel, the inner diameter of the blood vessel, the wall thickness, and Wall-to-Lumen Ratio (WLR) and Wall Cross-Sectional Area (WCSA) following along arterial branches that are the object of measurement, as index values based on the wall thickness, based on the blood vessel boundary positions detected in S922, where the following hold.

$$WLR=(\text{outer diameter of blood vessel}-\text{inner diameter of blood vessel})/(\text{inner diameter of blood vessel})$$

$$WCSA=\pi((\text{outer diameter of blood vessel})^2-(\text{inner diameter of blood vessel})^2)$$

Step S942: Display

The display control unit 133 displays a graph on the monitor 305 of the outer diameter of the blood vessel, the inner diameter of the blood vessel, the wall thickness, and wall thickness index values, measured following along the blood vessel. That is to say, the position in the direction in which the blood vessel runs is displayed on the horizontal axis, and the outer diameter of the blood vessel, the inner diameter of the blood vessel, the wall thicknesses on the left and right sides, and wall thickness index values (WLR and WCSA) are displayed on the vertical axis. Note however, that the display method of measurement values and index values is not restricted to this, and that the type of measurement value or index value may be selected and the display switched. Displaying this sort of wall thickness graph facilitates user comprehension of wall thickness distribution along the blood vessel. The display control unit 133 also performs a superimposed display of the wall boundaries detected in S922 following along the blood vessel, and the measurement values and wall thickness index values measured in S932, upon a confocal image or non-confocal image, or a composited image thereof. The measurement values and wall thickness index values may be displayed in grayscale or may be displayed as a color map correlated with an optional color bar. Displaying such a distribution of wall thicknesses as a map facilitates user comprehension of wall thickness values at the fundus.

Although description has been in the present embodiment made regarding a case where the deciding unit 131 performs inter-image computation and extracts image features (photoreceptor detection, blood vessel wall boundary detection, etc.) based on image features and disorder candidate regions, and decides the method regarding image measurement the present invention is not restricted to this. For example, an arrangement where the determining unit 1311 of the deciding unit 131 determines which image to read into the storage unit 120 or which image to display on the monitor 305, based on image features and disorder candidate regions, is also included in the present invention. Further, the image processing method deciding unit 1312 may decide the image display method (resolution, number of gradients, number of frames (including whether a moving image or still image), etc.) based on image features and disorder candidate regions.

According to the above-described configuration, The information processing apparatus 10 performs the following processing on images taken by an SLO apparatus to acquires confocal images and non-confocal images at generally the same time. Based on image features and disorder candidate regions acquired in the images, the more crucial a portion for observation or image analysis included in an image is, the wider the variety or greater the detail of images that are generated is, or a wider variety of images are measured. Accordingly, eye images that are crucial for observation and analysis can be efficiently generated or measured.

Third Embodiment: Deciding Image Processing Method by Image Analysis Results

An information processing apparatus according to a third embodiment is configured to decide an image generating method or measuring method based on not only image attributes or image features (disorder candidates) acquired from the image, but also analysis results from analyzing the image, which is to say image quality, and percentage of an imaging object region in an image. Specifically, description will be made regarding an image generating method or measuring method in a case where the same retinal blood vessels are taken as confocal images Dcj and two types of non-confocal images Dnk (non-confocal images taken with the aperture opened to a large diameter and moved to the right side and left side along the retinal blood vessels). The configuration of apparatuses connected to the information processing apparatus 10 according to the present embodiment is the same as in the case in the second embodiment. Note however, than the reception method of confocal signals and non-confocal signals by the SLO imaging apparatus 20 in the present embodiment differs, in that a configuration is made to where the diameter and position of the aperture (pinhole) is variable, so as to be able to receive as confocal signals as in FIG. 3C or to be able to enlarge the diameter of aperture as in FIG. 3D and to move the aperture so as to receive non-confocal signals.

Figure 10:
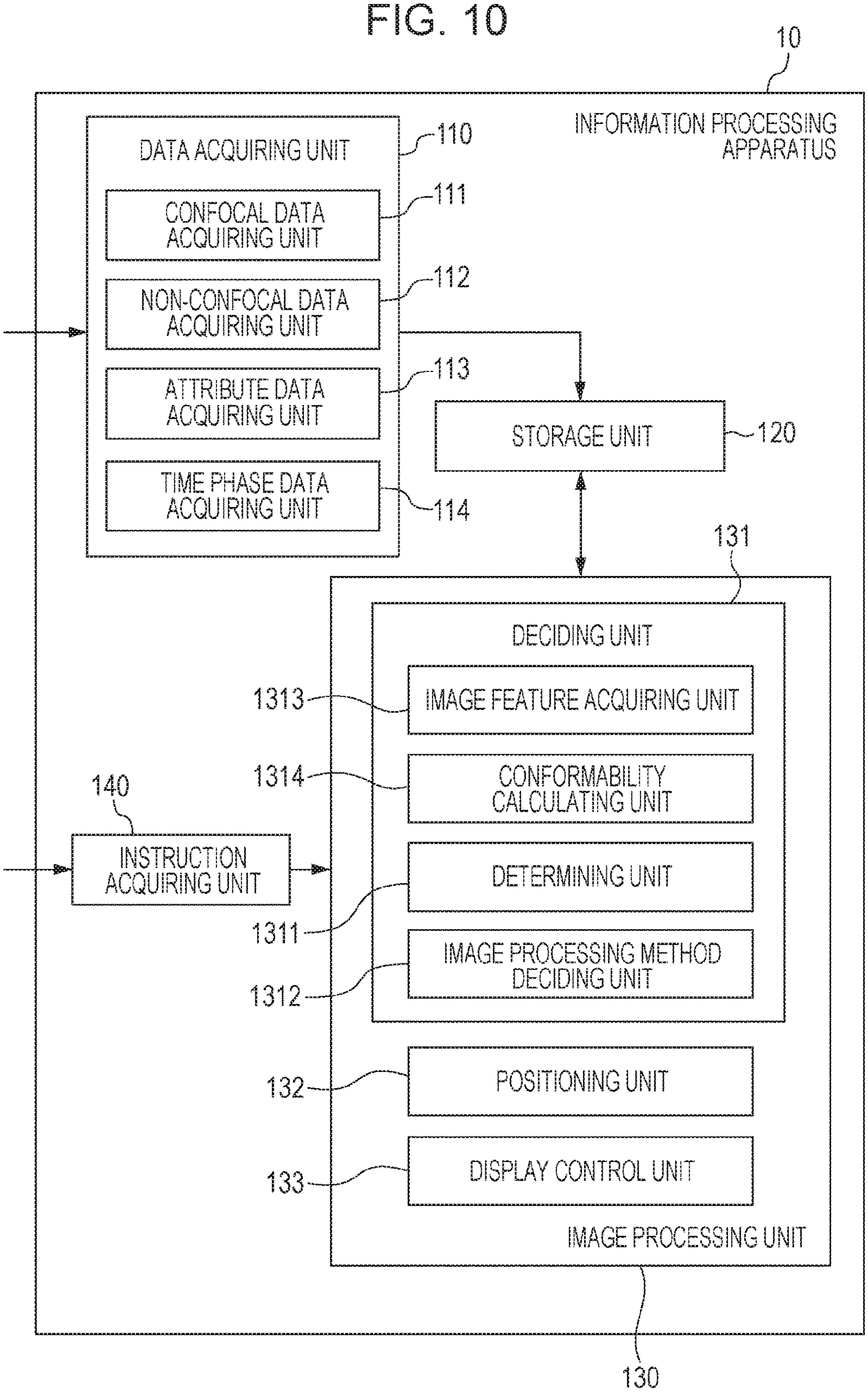
FIG. 10 is a block diagram illustrating a functional configuration example of an information processing apparatus according to a third embodiment.

FIG. 10 is a functional block diagram of the information processing apparatus 10 according to the present embodiment, which differs from the arrangement in the second embodiment with regard to the point that the deciding unit 131 includes a conformability calculating unit 1314. The image processing flow according to the present embodiment is the same as in FIG. 5, and is the same as the second embodiment except for S510, S520, and S530. Accordingly, S510, S520, and S530 will be described in the present embodiment.

Step S510: Acquiring Images

The image acquiring unit 110 requests the SLO image imaging apparatus 20 and time phase data acquisition apparatus 50 to acquire wide-angle images Dcl and Dnl, confocal image Dcj, and two types of non-confocal images (Dnr and Dnl) at the imaging position as in the second embodiment, and corresponding attribute data and fixation target positions F1 and Fcn, and time phase data. Attribute data in the present embodiment is date of image acquisition, position of acquisition, focus position, image type (confocal/R channel/L channel/optional inter-image-type computation), number of gradations, field angle, resolution, and number of frames. In response to this acquisition request, the SLO imaging apparatus 20 and time phase data acquisition apparatus 50 acquire the wide-angle images Dlc, Dlr, and Dll, confocal images Dcj, and non-confocal images Dnrk and Dnlk, and corresponding attribute data and fixation target positions Fl and Fcn, and time phase data Sj, and transmits these. The data acquiring unit 110 receives the wide-angle images Dlc, Dlr, and Dll, confocal images Dcj, and non-confocal images Dnrk and Dnlk, and corresponding attribute data and fixation target positions Fl and Fcn, and time phase data Sj, from the SLO imaging apparatus 20 and time phase data acquisition apparatus 50 via the LAN 30, and stores these in the storage unit 120. Hereinafter, of the two types of non-confocal images, images acquired by moving the aperture to the right side of the retinal blood vessels will be denoted by Dnr, and images acquired by moving the aperture to the left side of the retinal blood vessels will be denoted by Dnl. These images are acquired with the aperture (pinhole) opened wide.

Step S520: Generating Images

The image feature acquiring unit 1313 acquires the retinal blood vessel regions and arteriovenous crossing portions as image features from the wide-angle images Dln. Further, the conformability calculating unit 1314 calculates the conformability based on the image quality of acquired image, and the percentage that the region actually imaged occupies in the region to be imaged, and the determining unit 1311 and image processing method deciding unit 1312 determine the image generating method based on the image features and conformability. The image processing unit 130 generates images based on the decision made by the image processing method deciding unit 1312. Further, the positioning unit 132 performs image positioning, and the display control unit 133 displays confocal images and non-confocal images. Specific image generating processing will be described in detail in S1110 through S1150 of FIG. 11A. Note that an arrangement may be made where the attribute acquiring unit 113 acquires the attribute data rather than the image feature acquiring unit 1313 acquiring image features in this step.

Step S530: Deciding Measurement Method

The image processing method deciding unit 1312 decides the measurement method based on the image features (or attribute data) and conformability of the image acquired in S520. Specific measurement method deciding processing will be described in detail in S1111, S1121, and S1131.

Figure 11A:
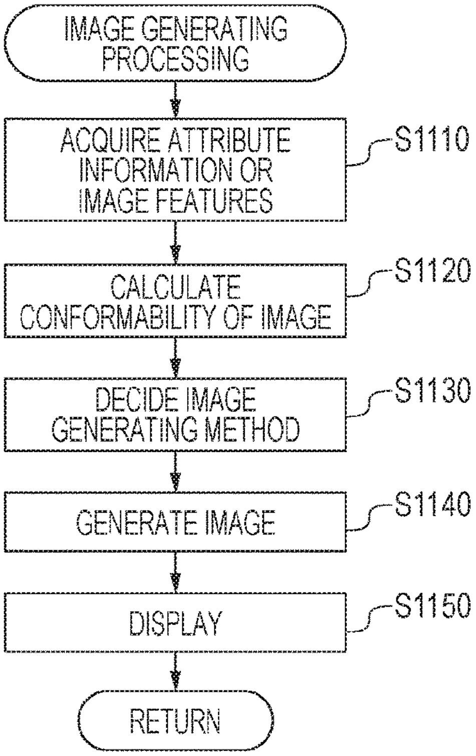
FIGS. 11A through 11D are flowcharts illustrating the details of processing executed in S520 and S530 according to the third embodiment and a fourth embodiment.

Next, the processing executed in S520 will be described in detail with reference to the flowchart illustrated in FIG. 11A.

Step S1110: Acquiring Attribute Information and Image Features

The image feature acquiring unit 1313 acquires retinal blood vessel regions and arteriovenous crossing portions as image features from the wide-angle images Dln. The method of acquiring the retinal blood vessel regions and arteriovenous crossing portions is the same as in the second embodiment, so description will be omitted. Cases where the image feature acquiring unit 1313 acquires photoreceptor defect regions from the confocal image Dcj as image features as in step S910 in the second embodiment are also included in the present invention. The specific method of acquiring photoreceptor defect region is the same as in the second embodiment, so description will be omitted. Also, an arrangement may be made where the attribute acquiring unit 113 acquires attribute data in this step, instead of the image feature acquiring unit 1313 acquiring image features. Attribute data in the present embodiment is date of image acquisition, position of acquisition, focus position, image type (confocal/R channel/L channel/optional inter-image-type computation), number of gradations, field angle, resolution, and number of frames.

Step S1120: Calculating Image Conformability

The conformability calculating unit 1314 calculates the conformability based on the image quality of each image, and the percentage of the region actually imaged occupies in the region to be imaged. For image quality, the signal-to-noise (S/N) ratio is calculated. The index of the image quality is not restricted to this, and any known index may be used. For example, Contrast-Noise Ratio (CNR) may be calculated. Also, a value indicating whether the region to be imaged has been sufficiently imaged is calculated by (area of region imaged in all frames)/(area of region to be imaged). In the present embodiment, conformability is expressed as $\omega 1 \cdot Iq + \omega 2 \cdot Ic$, where Iq is 1 if the S/N ratio is equal to or larger than a threshold T3, and is 0 if the S/N ratio is smaller than threshold T3. Ic is (area of region imaged in all frames)/(area of region to be imaged). ω1 and ω2 are weighting parameters that can be specified optional values in the range of 0 to 1. Both are 0.5 in the present embodiment.

Step S1130: Deciding Image Generating Method

The determining unit 1311 determines which imaged image (image for generating) to use to generate an image, based on the image features acquired by the image feature acquiring unit 1313 in S1110 and conformability calculated by the conformability calculating unit 1314 in S1120. Further, the image processing method deciding unit 1312 decides the image generating method (type of computation between images, and number of gradations, resolution, and number of frames of the image to be generated), based on the image features and conformability. The determining unit 1311 determines an R channel image Dnr and L channel image Dnl, including a retinal blood vessel region, that have a conformability or threshold T4 or higher, to be the object of generating. The image processing method deciding unit 1312 generates, with regard to images Dnr and Dnl including an arteriovenous crossing portion out of the images for generating, a 16-bit moving image of (R+L) image Dnr+l having the same resolution as the original image, and a composited image having the same resolution as the original image in 16-bit, and on the other hand, with regard to images Dnr and Dnl not including an arteriovenous crossing portion, an 8-bit composited image of (R+L) image Dnr+l having the same resolution as the original image in 8-bit.

In a case of the image feature acquiring unit 1313 acquiring a photoreceptor defect region as image features, as in S910 in the second embodiment, the following processing is performed. The determining unit 1311 determines all confocal images, and non-confocal images Dnk at the same imaging positions as confocal images Dcj containing photoreceptor defect regions, to be images for generating (imaging position and image type). Further, the image processing method deciding unit 1312 decides to generate a composited image having the same resolution as the original image in 16-bit using the confocal images included in the images for generating. The image processing method deciding unit 1312 also decides to generate a Split Detector image using a generating R channel image and L channel image included in the images for generating, in 16-bit as a composited image having the same resolution as the original image in 16-bit. However, this is not restrictive, and any image type to be generated and any generating method thereof may be specified, as long as an image generating method that enables a greater number of images to be observed and measured, or measure in detail, with regard to images that are crucial for observation and measurement.

Step S1140: Generating Images

The image processing unit 130 generates an image by performing computation among confocal images (Dln or Dn) using the images for generating determined by the determining unit 1311 in S1130 and the image generating method decided by the image processing method deciding unit 1312. Further, the positioning unit 132 performs image positioning. Specific image generating procedures that the image processing unit 130 performs in this step are the same as in the second embodiment, except for the point that the image for generating determined based on conformability (or the decided image generating method) differs, so detailed description will be omitted.

Figure 11B:
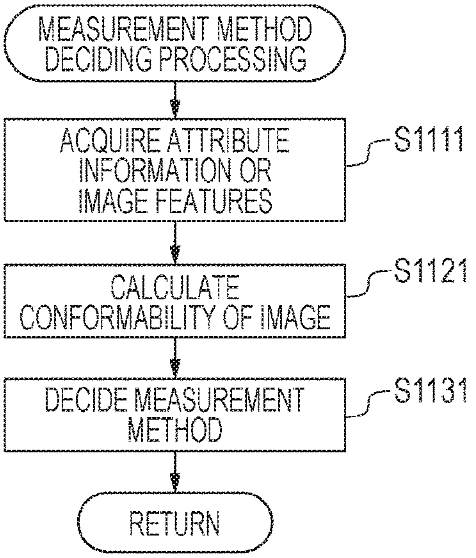

Next, the processing performed in S530 will be described in detail with reference to the flowchart illustrated in FIG. 11B.

Step S1111: Acquiring Attribute Information and Image Features

The image processing unit 130 references the attribute data acquired by the attribute acquiring unit 113 or the image features acquired by the image feature acquiring unit 1313 in S1110.

Step S1121: Calculating Image Conformability

The image processing unit 130 references the conformability calculated by the conformability calculating unit 1314 in S1120.

Step S1131: Deciding Measurement Method

The determining unit 1311 performs determination (imaging position and image type) of the images that are objects of measurement, based on image features acquired in S1111. Next, the image processing method deciding unit 1312 decides the image generating method (type of image processing, range of image processing and intervals of image processing) for the images that are objects of measurement. In the present embodiment, the number of images for generating have already been narrowed down (Dnr and Dnl that have conformability of threshold T4 or higher determined to be images for generating) based on conformability in the image generating method deciding processing (S1130), so the objects of measurement are not narrowed down further based on conformability in this step. Accordingly, the image processing method deciding unit 1312 decides Edge preservation smoothing processing
Blood vessel wall boundary detection
Blood vessel wall thickness measurement to be types of image processing to be performed on the (R+L) images Dr+l at imaging positions including arteriovenous crossing portions, having conformability of threshold T4 or higher. With regard to the range of image processing, edge preservation smoothing is performed for the entire image, and blood vessel wall boundary detection and blood vessel wall thickness measurement are decided only for arterial branches crossing veins. The image processing interval is decided to be in 1-pixel increments. Note that an arrangement may be made where no narrowing down of the images for generating is performed based on conformability at the time of deciding the image generating method in S1130, and instead the images that are the object of measurement may be narrowed down in this step based on conformability (along with the condition of images having conformability of threshold T4 or higher). Further, a configuration may be made where different conformability conditions may be set in the image generating method deciding processing in S1130 and this step, and measurement is performed on images satisfying both.

While the conformability has been described as being calculated by the conformability calculating unit 1314 based on the image quality and the percentage including the region to be imaged, the calculating method of conformability is not restricted to this, and any calculating method may be used as long as based on coordinates and pixel values of the imaged images. For example, the conformability may be calculated based on luminance characteristics of the imaged images, i.e., luminance values and statistics relating to the luminance values. Specifically, the average luminance value of the image that has been imaged may be calculated, and a value where this average luminance value is weighted may be used as the conformability. Alternatively, the contrast of the imaged images (maximum luminance−minimum luminance)/(maximum luminance+minimum luminance) may be calculated as conformability.

Although an arrangement has been described in the above embodiment where the deciding unit 131 performs inter-image computation and extracts features (photoreceptor detection, blood vessel wall boundary detection, etc.) based on image attributes or image features and image acquisition results (image quality, etc.), and decides a method relating to image measurement, the present invention is not restricted to this. For example, arrangements where the determining unit 1311 in the deciding unit 131 determines which image to read into the storage unit 120 or which image to display on the monitor 305, based on image attributes or image features and image acquisition results (image quality, etc.), are also included in the present invention. Alternatively, the image processing method deciding unit 1312 may decide methods to display images (resolution, number of gradients, number of frames (including deciding whether moving image or still image), etc.), based on image attributes or image features and image acquisition results (image quality, etc.).

According to the configuration described above, the information processing apparatus 10 decides generating methods and measuring methods for image using not only image attributes or image features (disorder candidates) acquired from the images, but also using image acquisition results, i.e., image quality and percentage including region to be imaged. Thus, images of the eye that are crucial for observation and measurement can be efficiently generated or measured.

Fourth Embodiment: Deciding Image Processing Method Based on Processing Results by Examination Date The information processing apparatus 10 according to the present embodiment is configured such that, based on images acquired on different examination dates, the more examination dates including a reference examination date that generating and measurement have been performed there are in attributes of an image, the easier to is for that image to be determined to be an image for generating or an image for measurement. Specifically, in a case where confocal images and corresponding non-confocal images including a photoreceptor outer segment defect region have been acquired on different examination dates, the attributes of these image groups taken on different examination dates are acquired, the following processing is performed. That is to say, description will be made regarding a case where the more examination dates including a reference examination date that generating and measurement have been performed there are in attributes of an image, the easier to is for that image to be determined to be an image for generating or an image for measurement. The configuration of apparatuses connected to the information processing apparatus 10 according to the present embodiment is as illustrated in FIG. 2A, and differs from the third embodiment with regard to the point no time phase data acquisition apparatus is connected. The functional block configuration of the information processing apparatus 10 according to the present embodiment differs from that in the third embodiment with regard to the points that the data acquiring unit 110 does not have the time phase acquiring unit 114, the data acquiring unit 110 acquires examination data of different examination dates, the deciding unit 131 does not have the image feature acquiring unit 1313, and the conformability calculating unit 1314 calculates conformability as to base examination images based on the attributes of images on different examination dates.

Figure 5:
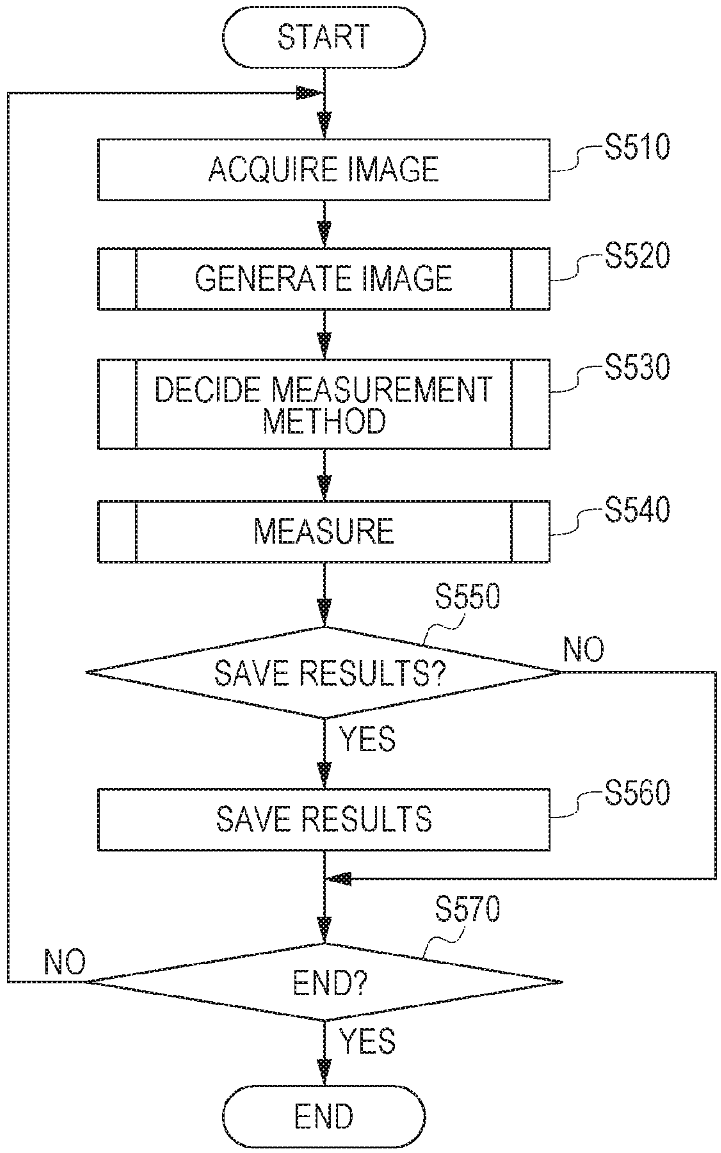
FIG. 5 is a flowchart of processing which the information processing apparatus according to the first embodiment executes.

The image processing flow according to the present embodiment is illustrated in FIG. 5, and is the same as the third embodiment except for S510, S520, and S530. Accordingly, S510, S520, and S530 will be described in the present embodiment.

Step S510: Acquiring Images

The data acquiring unit 110 requests the data server 40 to transfer past confocal images Dcjf (where f=1, 2, . . . , e−1, f being a natural number indicating the No. of the examination in serial order), past non-confocal images Dnkf, and fixation target positions Fcnf. The data server 40 transfers the data corresponding to the request to the information processing apparatus 10, and the data is saved in the storage unit 120. In the present embodiment, e=5, and Split Detector images Dnsf are acquired as non-confocal images Dnkf of past examinations.

Next, the data acquiring unit 110 requests the SLO imaging apparatus 20 for acquisition of wide-angle images Dlce and Dlne, confocal images Dcje and non-confocal images Dnke, and fixation target positions Fle and Fcne corresponding to the newest examination. In the present embodiment, the wide-angle images Dlce and Dlne, confocal images Dcje, and non-confocal images Dnke are acquired with fixation target positions Fle at the fovea and fixation target positions Fcne at the fovea and parafovea. Note that the imaging position setting method is not restricted to this, and the imaging position may be set to an optional position. The SLO imaging apparatus 20 acquires and transmits the wide-angle images Dlce and Dlne, confocal images Dcje and non-confocal images Dnke, and fixation target positions Fle and Fcne, in response to the acquisition request. The data acquiring unit 110 receives the wide-angle images Dlce and Dlne, confocal images Dcje, non-confocal images Dnke, and fixation target positions Fle and Fcne, from the SLO imaging apparatus 20 via the LAN 30. The data acquiring unit 110 stores the received wide-angle images Dlce and Dlne, confocal images Dcje, non-confocal images Dnke, and fixation target positions Fle and Fcne in the storage unit 120.

Step S520: Generating Images

Upon the attribute acquiring unit 113 having acquired attribute data for all examination images, and the conformability calculating unit 1314 having calculating the conformability with past examination images, the determining unit 1311 and image processing method deciding unit 1312 decide images for generating and image generating method, based on the conformability. The image processing unit 130 generates images based on the decision of the determining unit 1311 and image processing method deciding unit 1312. Further, the positioning unit 132 performs positioning, and the display control unit 133 displays confocal images and non-confocal images. Specifics of the image generating processing will be described in detail in S1112, S1122, S1132, S1142, and S1152.

Step S530: Deciding Measurement Method

Upon the conformability calculating unit 1314 having calculated the conformability of the images of the current examination with the past examination images based on attribute data of the past examination images, the determining unit 1311 and image processing method deciding unit 1312 decide images for measuring and measuring method, based on the conformability. Specifics of the measurement method deciding processing will be described in detail in S1113, S1123, and S1132.

Figure 11C:
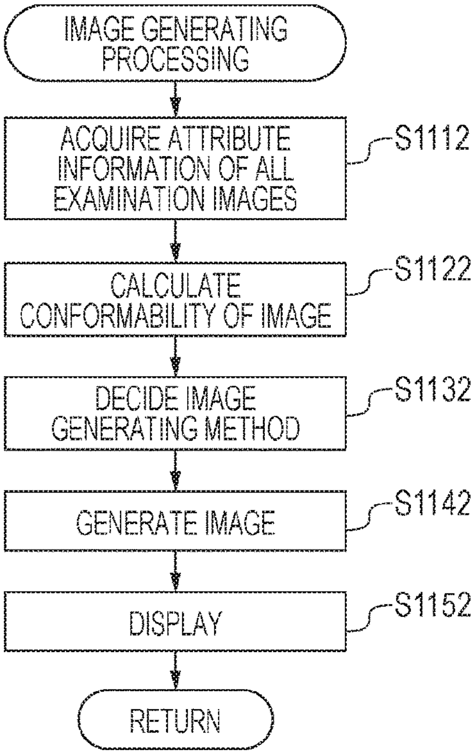

Next, the processing performed in S520 will be described in detail with reference to the flowchart illustrated in FIG. 11C.

Step 1112: Acquiring Attribute Information of all Examination Images

The attribute acquiring unit 113 acquires attribute data relating to the past examination images and the current examination images. Attribute data in the present embodiment is date of image acquisition, position of acquisition, focus position, image type (confocal/R channel/L channel/optional inter-image-type computation), number of gradations, field angle, resolution, and number of frames.

Step 1122: Calculating Inter-Examination Conformability

The conformability calculating unit 1314 calculates conformability with past examination images for each image, based on the attribute data of past examination images. In the present embodiment, conformability of the current examination images as to the past examination images is calculated by $\omega 3 \cdot Ib + \omega 4 \cdot \Sigma Ien$ for each of the current examination images. Ib here is a value (0 or 1) representing whether or not there is an image having the same attributes other than the date of acquisition in a reference examination (baseline). Ien is calculated by (value (0 or 1) representing whether or not there is an image having the same attributes other than the date of acquisition)/(total number of past examinations). Σ represents the summation of all past examinations. ω3 and ω4 are weighting parameters that can be given optional values in the range of 0 to 1. Both are 0.5 in the present embodiment.

Step 1132: Deciding Image Generating Method

The determining unit 1311 determines an image for generating based on the conformability with past examination images calculated in S1122, and the image processing method deciding unit 1312 decides an image generating method. In the present embodiment, the determining unit 1311 determines that images of which the conformability calculated in S1122 is equal to or larger than a threshold T5 use confocal images Dcj and Split Detector images Dnsk as images for generating, and images of which the conformability calculated in S1122 is smaller than threshold T5 use only confocal images Dcj as images for generating. Also, the image processing method deciding unit 1312 decides to generate the former as 16-bit moving images and composited images, and the later as 16-bit composited images having half the resolution of the original image. The determination of images for generating and image generating methods based on the calculated conformability is not restricted to the procedures described here. Any determination of images for generating and image generating method determination may be performed as long as the more examination dates including a reference examination date that generating and measurement have been performed there are in attributes of an image, the easier to is for that image to be determined to be an image for generating or an image for measurement.

Step 1142: Generating Images

The image processing unit 130 generates an image based on the decision that the image processing method deciding unit 1312 has made in S1132. Next, the positioning unit 132 performs inter-frame positioning on the wide-angle images Dlcf (where f=1, 2, . . . , e) for each examination data, and confocal images Dcjf. The specific procedures for positioning frames are the same as in S520 in the first embodiment, so description will be omitted. Next, the positioning unit 132 performs inter-frame positioning of the wide-angle images Dlnf and non-confocal images Dbkf, using the positioning parameter values decided for the wide-angle images Dlcf and confocal images Dcjf. The positioning unit 132 performs positioning among the wide-angle images Dlcf (where f=1, 2, . . . , e) for each examination data, and the confocal images Dcjf, and calculates the relative position of the confocal images Dcjf upon the wide-angle images Dlcf. In a case where there is an overlapping region among confocal images Dlcf, first, the inter-image similarity is calculated relating to the overlapping region, and the confocal images Dcjf are positioned at the position where the inter-image similarity is the greatest. In a case where images of three or more different types of magnification have been acquired in S510, positioning is performed in order from lower-magnification images. Any known technique may be used for the inter-image similarity and coordinate conversion techniques. Positioning is performed in the present embodiment using correlation coefficients for inter-image similarity, and Affine transformation as the coordinate transform technique. A tiled image of confocal images Dcjf is generated using the information of relative positions of the confocal images Dcjf on the wide-angle images Dlcf obtained by this positioning processing. Next, the positioning unit 132 generates a tiled image of non-confocal images Dnkf using the information of relative positions of the confocal images Dcjf on the wide-angle images Dlcf.

Further, positioning is performed between reference wide-angle images and wide-angle images Dlcf and Dlnf other than the reference wide-angle images. The reference wide-angle images, confocal images, and non-confocal images, can be selected from any examination date of images acquired in S510. In the present embodiment, an image group of the oldest examination date (wide-angle images Dlc1 and Dln1, confocal images Dcj1, and non-confocal images Dnk1) are each taken as reference images.

The relative position of the reference image Dlc1 as to the reference image Dcj1, the relative position of other examination images as to the reference image Dlc1, and the relative position of the confocal images Dcjf as to the images Dlcf, are used to find the relative position of the confocal images Dcjf as to the reference image Dcj1. Note that the reference images Dcj1 and Dcjf may be directly positioned. Any known technique may be used for positioning. Positioning is performed in the present embodiment using Affine transformation as primary general positioning. Next, free form deformation (FFD), which is a type of a non-rigid positioning technique, is used to perform detailed positioning. In either positioning, correlation coefficients are used for inter-image similarity. Of course, this is not restrictive, and any known image similarity technique may be used. Next, the positioning unit 132 uses information the relative position of the confocal images Dcjf as to the reference image Dcj1 to find the relative position of the non-confocal images Dnkf as to the reference image Dck1.

Thus, the pixels of the reference images (Dlc1, Dln1, Dcj1, and Dnk1) and the images (Dlcf, Dlnf, Dcjf, and Dnkf) other than the reference images are correlated. Note that the present invention is not restricted to positioning based on similarity of pixel values, and an arrangement may be made where blood vessel regions are identified, upon which positioning is performed based on features using the identified blood vessel regions.

Step 1152: Display

The display control unit 133 displays the image group generated so far on the monitor 305. Here, the composited images are displayed tiled using the above-described positioning parameters. Also, composited images, and in a case where moving images have been generated, inter-frame-positioned moving images, are displayed regarding a imaging position instructed via the instruction acquiring unit 140.

Figure 11D:
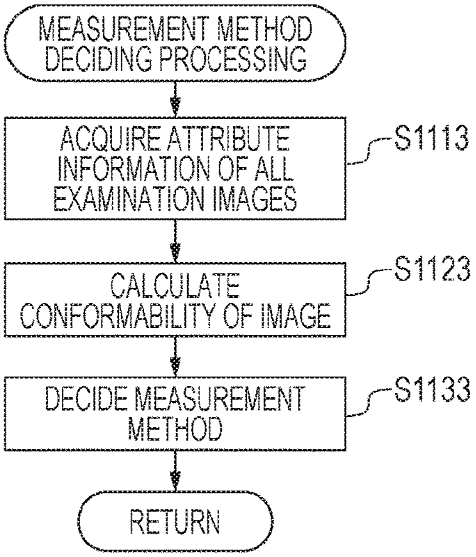
Figure 12:
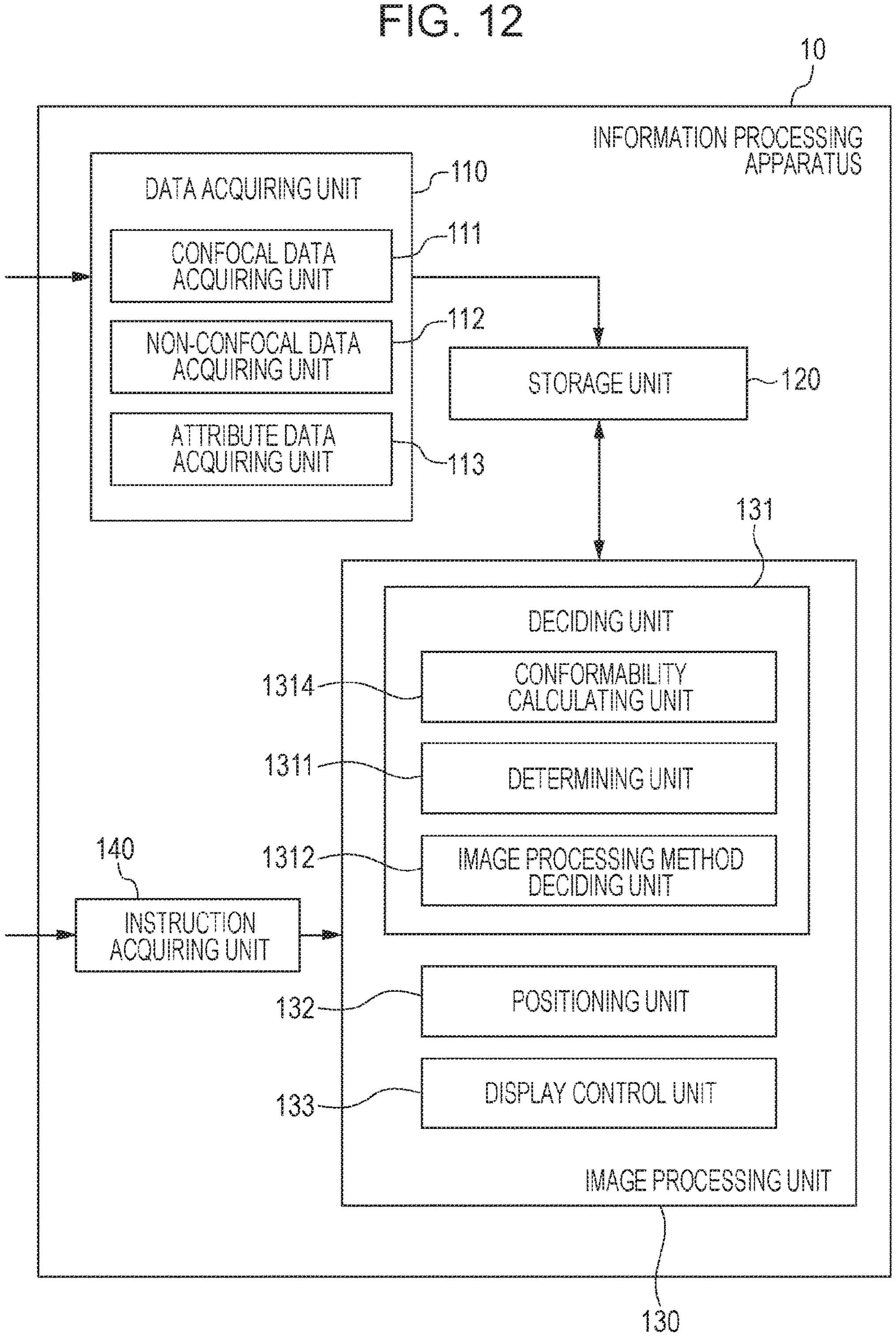
FIG. 12 is a block diagram illustrating a functional configuration example of an information processing apparatus according to the fourth embodiment.

Next, the processing performed in S530 will be described in detail with reference to the flowchart illustrated in FIG. 11D.

Step 1113: Acquiring Attribute Information of All Images

The image processing unit 130 references the attribute data of all examination images acquired by the attribute acquiring unit 113 in S1112.

Step 1123: Calculating Inter-Examination Conformability

The image processing unit 130 references the conformability calculated by the conformability calculating unit 1314 in S1122.

Step 1133: Deciding Measurement Method

The determining unit 1311 determines images to be measured (imaging position and image type) based on the inter-examination conformability referenced in S1123, and the image processing method deciding unit 1312 decides the image generating method (type of image processing, range of image processing, and interval of image processing). Further, there is the need for the image processing method deciding unit 1312 to perform measurement on two types of images and compare the measurement results regarding Detection of photoreceptor position Creating a Voronoi diagram Measuring photoreceptor density under the same conditions, so both images are processed over the same measurement range as the original image, in one-pixel intervals. However, this is not restrictive, and any type of image processing, range of image processing, and interval of image processing may be measured for each image, as long as processing that enables more detailed measurement with regard to images that are crucial for measurement.

Although description has been made in the above embodiment where the deciding unit 131 decides methods relating to inter-image computation and image feature extraction (photoreceptor detection, blood vessel wall boundary detection, etc.), and image measurement, based on the degree of having attributes where more examination dates on which generating and measurement have been performed, the present invention is not restricted to this. For example, arrangements where the determining unit 1311 in the deciding unit 131 determines which image to read into the storage unit 120 or which image to display on the monitor 305, based on the degree of having attributes where more examination dates on which generating and measurement have been performed, are also included in the present invention. Alternatively, the image processing method deciding unit 1312 may decide methods to display images (resolution, number of gradients, number of frames (including deciding whether moving image or still image), etc.), based on the degree of having attributes where more examination dates on which generating and measurement have been performed.

According to the information processing apparatus 10 configured as described above, based on images acquired on different examination dates, the more examination dates including a reference examination date that generating and measurement have been performed there are in attributes of an image, the easier to is for that image to be determined to be an image for generating or an image for measurement. Accordingly, in a case of comparing and observing images of different examination dates, eye images that are crucial for observation and analysis can be efficiently generated or measured.

OTHER EMBODIMENTS

Although description has been made that the data acquiring unit 110 includes both the confocal data acquiring unit 111 and the non-confocal data acquiring unit 112, the data acquiring unit 110 does not need to include the non-confocal data acquiring unit 112, as long as the configuration enables acquisition of two or more types of non-confocal data.

OTHER EMBODIMENTS

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-093540, filed Apr. 30, 2015, which is hereby incorporated by reference herein in its entirety.

What is claimed is:

1. An information processing apparatus comprising:

a deciding unit configured to decide, based on an analysis result of one of a confocal image of an eye and a non-confocal image of the eye, whether or not to analyze perform at least one of generation and analysis of the other; and a display control unit configured to display at least one of a generation result of the other and an analysis result of the other on a display unit, in a case where it is decided to perform at least one of generation and analysis of the other.

2. The information processing apparatus according to claim 1, further comprising:

a determination unit configured to determines a state of an object of observation in the confocal image by analyzing the confocal image, wherein the deciding unit decides whether or not to perform at least one of generation and analysis of the non-confocal image based on the state of the object of observation.

3. The information processing apparatus according to claim 2, wherein the state of the object of observation is whether or not there is a disorder region in the confocal image, and in a case where there is a disorder region, the deciding unit decides to perform at least one of generation and analysis the non-confocal image.

4. The information processing apparatus according to claim 3, wherein whether or not there is a disorder region is whether or not there is a photoreceptor defect region in the confocal image, and in a case where there is a photoreceptor defect region in the confocal image, the deciding unit decides to perform at least one of generation and analysis of the non-confocal image.

5. The information processing apparatus according to claim 1, further comprising:

an image acquiring unit configured to acquire a plurality of types of images of an eye, including the confocal image and the non-confocal image of the eye, wherein the information processing apparatus is communicably connected to an ophthalmologic imaging apparatus that captures a plurality of types of images of the eye, and wherein the image acquiring unit acquires the plurality of types of images obtained by imaging the eye at generally the same time.

6. The information processing apparatus according to claim 5, wherein the ophthalmologic imaging apparatus includes a shared light source to acquire a confocal image and a non-confocal image of the eye, and an optical member that splits returning light from the eye irradiated by light form the light source, into returning light passing through a confocal region and returning light passing through a non-confocal region, and wherein the image acquiring unit acquires the confocal image based on the returning light passing through the confocal region, and acquires the non-confocal image based on the returning light passing through the non-confocal region.

7. The information processing apparatus according to claim 6, wherein the image acquiring unit acquires the confocal image and non-confocal image of the eye, obtained by adjusting at least one of a position and a shape of an aperture disposed upstream of a light-receiving portion that receives light of at least one of returning light passing through the confocal region and returning light passing through the non-confocal region.

8. The information processing apparatus according to claim 6, wherein an acquisition position of the confocal image and an acquisition position of the non-confocal image of the eye are the same.

9. An operation method of an information processing apparatus, the method comprising:

deciding, based on an analysis result of one of a confocal image of an eye and a non-confocal image of the eye, whether or not to perform at least one of generation and analysis of the other; and displaying at least one of a generation result of the other and an analysis result of the other on a display unit, in a case where it is decided to perform at least one of generation and analysis of the other.

10. The operation method of the information processing apparatus according to claim 9, the method further comprising:

determining a state of an object of observation in the confocal image by analyzing the confocal image;

wherein, based on the state of the object of observation, it is decided whether or not to perform at least one of generation and analysis of the non-confocal image.

11. The operation method of the information processing apparatus according to claim 10, wherein the state of the object of observation is whether or not there is a disorder region in the confocal image, and in a case where there is a disorder region, the deciding decides to perform at least one of generation and analysis of the non-confocal image.

12. The operation method of the information processing apparatus according to claim 11, wherein whether or not there is a disorder region is whether or not there is a photoreceptor defect region in the confocal image, and in a case where there is a photoreceptor defect region, the deciding decides to perform at least one of generation and analysis of the non-confocal image.

13. A non-transitory computer-readable storage medium storing a program for causing a computer to execute the method according to claim 9.

14. The information processing apparatus according to claim 1, wherein, in a case where at least the confocal image is an image obtained by imaging photoreceptors of the eye, the display control unit causes the display unit to display at least one of a generation result of the confocal image and an analysis result of the confocal image.

15. The information processing apparatus according to claim 1, wherein, in a case where at least the non-confocal image is an image obtained by imaging a blood vessel of the eye, the display control unit causes the display unit to display at least one of a generation result of the non-confocal image and an analysis result of the non-confocal image.

* * * * *